United States Patent
Antonyshyn et al.

(10) Patent No.: US 8,974,535 B2
(45) Date of Patent: Mar. 10, 2015

(54) METHOD OF FORMING PATIENT-SPECIFIC IMPLANT

(75) Inventors: Oleh Antonyshyn, Toronto (CA); Glenn Edwards, Toronto (CA); James Mainprize, Toronto (CA)

(73) Assignee: Sunnybrook Health Sciences Centre, Toronto, Ontario (CA)

( * ) Notice: Subject to any disclaimer, the term of this patent is extended or adjusted under 35 U.S.C. 154(b) by 444 days.

(21) Appl. No.: 13/158,247

(22) Filed: Jun. 10, 2011

(65) Prior Publication Data

US 2012/0010711 A1    Jan. 12, 2012

Related U.S. Application Data

(60) Provisional application No. 61/353,925, filed on Jun. 11, 2010.

(51) Int. Cl.
*A61F 2/30* (2006.01)
*A61F 2/28* (2006.01)

(52) U.S. Cl.
CPC .......... *A61F 2/30942* (2013.01); *A61F 2/2875* (2013.01); *A61F 2002/3096* (2013.01)
USPC .................................. 623/17.18

(58) Field of Classification Search
CPC ............ A61B 10/02; A61B 17/00234; A61B 17/0218; A61F 2/2418; A61N 1/05; A61N 7/022
USPC ........ 623/17.18–17.19; 606/69, 86 R, 92–94, 606/279, 285, 903
See application file for complete search history.

(56) References Cited

U.S. PATENT DOCUMENTS

| | | | |
|---|---|---|---|
| 5,370,692 A | 12/1994 | Fink et al. | |
| 5,380,328 A * | 1/1995 | Morgan | 606/70 |
| 5,741,215 A | 4/1998 | D'Urso | |
| 6,379,816 B1 * | 4/2002 | De Loose et al. | 428/608 |

(Continued)

FOREIGN PATENT DOCUMENTS

| | | |
|---|---|---|
| DE | 10006851 A1 | 8/2001 |
| EP | 1806113 A1 | 7/2007 |

(Continued)

OTHER PUBLICATIONS

Rotaru et al. Silicone rubber mould cast polyethylmethacrylate-hydroxyapatite plate used for repairing a large skull defect. Journal of Cranio-Maxillofacial Surgery. (2006). vol. 34, pp. 242-246.

(Continued)

*Primary Examiner* — David Isabella
*Assistant Examiner* — Ann Schillinger
(74) *Attorney, Agent, or Firm* — Hill & Schumacher

(57) ABSTRACT

Methods and apparatus are provided for forming a patient-specific surgical implant based on mold system. The apparatus comprises a forming tool and a mold that may be generated using imaging and processing techniques and rapid prototyping methods. The mold apparatus includes at least two non-adjacent surface features for securing an implant forming material (such as a titanium mesh) during the forming process, enabling the implant forming material to be stretched beyond its elastic and thus permanently deformed with the correct patient-specific curvature. The implant may include one or more anatomic surface features for guidance and registration when transferring the implant to a patient.

31 Claims, 22 Drawing Sheets

(56) References Cited

U.S. PATENT DOCUMENTS

| | | | |
|---|---|---|---|
| 6,859,661 B2* | 2/2005 | Tuke | 600/424 |
| 6,932,842 B1 | 8/2005 | Litschko et al. | |
| 7,603,192 B2 | 10/2009 | Martin et al. | |
| 7,636,459 B2 | 12/2009 | Dore et al. | |
| 2002/0059049 A1 | 5/2002 | Bradbury et al. | |
| 2003/0030170 A1 | 2/2003 | Abe et al. | |
| 2003/0042641 A1 | 3/2003 | Abe et al. | |
| 2003/0109784 A1 | 6/2003 | Loh et al. | |
| 2004/0005423 A1* | 1/2004 | Dalton et al. | 428/36.9 |
| 2004/0117015 A1 | 6/2004 | Biscup | |
| 2004/0133276 A1 | 7/2004 | Lang et al. | |
| 2004/0138591 A1 | 7/2004 | Iseki et al. | |
| 2005/0021142 A1 | 1/2005 | Ganz et al. | |
| 2005/0133955 A1* | 6/2005 | Christensen | 264/219 |
| 2005/0148843 A1 | 7/2005 | Roose | |
| 2005/0288790 A1 | 12/2005 | Swords | |
| 2006/0008773 A1 | 1/2006 | Liao | |
| 2006/0136058 A1 | 6/2006 | Pietrzak | |
| 2006/0217813 A1 | 9/2006 | Posnick et al. | |
| 2007/0276501 A1 | 11/2007 | Betz et al. | |
| 2008/0257363 A1 | 10/2008 | Schoenefeld et al. | |
| 2009/0270868 A1 | 10/2009 | Park et al. | |
| 2009/0281623 A1 | 11/2009 | Kast et al. | |

FOREIGN PATENT DOCUMENTS

| | | |
|---|---|---|
| WO | 00/71083 | 11/2000 |
| WO | 01/85040 | 11/2001 |
| WO | 0185040 | 11/2001 |
| WO | 2004110309 | 12/2004 |
| WO | 2005032790 | 4/2005 |
| WO | 2007045000 | 4/2007 |
| WO | 2007139949 | 12/2007 |
| WO | 2011/101731 | 8/2011 |

OTHER PUBLICATIONS

Kuttenberger et al. Long-term results following reconstruction of craniofacial defects with titanium micro-mesh systems. Journal of Cranio-Maxillofacial Surgery. (2001) vol. 29, pp. 75-81.

Bell et al. Computer-Assisted Planning Stereolithographic Modeling, and Intraoperative navigation for Complex Orbital Reconstruction a Descriptive Study in a Preliminary Cohort. American Association of Oral and Maxillofacial Surgeons J Oral Maxillofac Surg. (2009) vol. 67 pp. 2559-2570.

Brandt et al. The Use of a Polyurethane Skull Replica as a Template for Contouring Titanium Mesh. J. Oral Maxillofac Surg. (2002) vol. 60. pp. 337-338.

Ridder et al. Individual Prefabricated titanium implants and titanium mesh in skull base reconstructive surgery. A report of cases. Eur Arch Otorhinolaryngol (2004) vol. 261. pp. 282-290.

Metzger et al. Semiautomatic Procedure for Individual Preforming of Titanium Meshes for Ordital Fractures. Plastic and Reconstructive Surgery Journal. Mar. 2007.

Wu et al. Computer-Aided Design for Three-Dimensional Titanium Mesh Used for Repairing Skull Base Bone Defect in Pediatric Neurofibromatosis Type 1. Pediatric Neurosurgery (2008) vol. 44. pp. 133-139.

Cabraja et al. Long-term results following titanium cranioplasty of large skull defects. Neurosurg Focus (2009) 26 (6):E10.

Tan et al. Research on the process of multi-point forming for the customized titanium alloy cranial prosthesis. Journal of Materials Processing Technology (2007) vol. 187-188, 453-457.

Murray et al. Optimizing Craniofacial Osteotomies Applications of Haptic and Rapid Prototyping Technology. J Oral Maxillofac Surg. (2008). pp. 1-59.

Murray et al. Provided for non-commercial research and education use. Not for reproduction, distribution or commercial use. JPRAS (2008). vol. 61. pp. 906-916.

Harun et al. Digital Approach in Reconstruction of Craniofacial Defect. IFMBE Proceedings vol. 4 Track 14.

Sauret et al. Computer assisted surgery: the use of digital images in enabling computerized design and manufacture of titanium implants. Imaging. (2002) vol. 14. pp. 464-471. No. 6.

http://www.nchc.org.tw/en/collaborative_research/medical_computing/medical_computing_3.php. Computer Assisted Prefabrication of a Cranioplasty Implant (National Center for High Performance Computing). Oct. 27, 2011.

International Search Report for PCT/CA2011/050357 mailed Oct. 25, 2011.

Supplementary European Search Report for European patent application No. 11791801.1, mailed May 21, 2014.

* cited by examiner

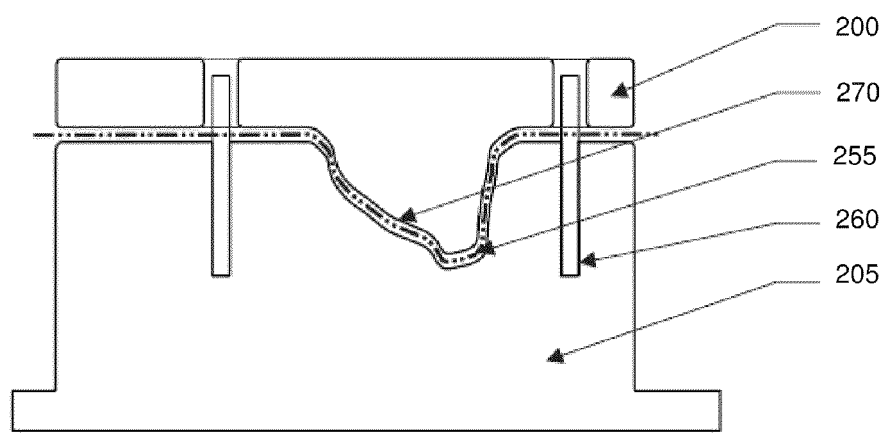
Figure 6(c)
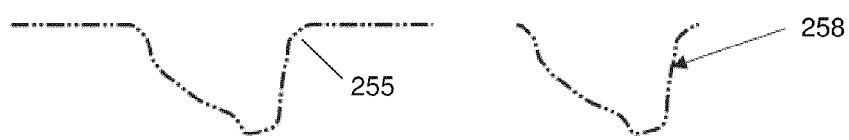
Figure 6(d)
Figure 6(e)

(a)

620
600
610

(b)

630

METHOD OF FORMING PATIENT-SPECIFIC IMPLANT

CROSS-REFERENCE TO RELATED APPLICATION

This application claims priority to U.S. Provisional Application No. 61/353,925, titled "METHOD OF FORMING PATIENT-SPECIFIC IMPLANT WITH TOPOLOGICAL CONTOURS" and filed on Jun. 11, 2010, the entire contents of which are incorporated herein by reference.

BACKGROUND

The present disclosure relates to methods and apparatus for the fabrication of patient-specific implants using imaging data, and more particularly relates to the fabrication of patient-specific implants for the reconstruction of defects of the skull and facial bones.

The surgical repair of a defect of the skull or facial bones can be a technically difficult, laborious and time-consuming procedure, and the accurate restoration of the missing anatomy can be particularly challenging. The recent adaptation of computer assisted design and rapid prototyping technology is known to dramatically increase efficiency and improve outcomes. Provided that the defect is stable, clearly defined and well visualized prior to surgery, computer modeling can be employed to generate a virtual 3D model of a patient-specific implant.

Titanium mesh in particular has proven to be effective clinically in the reconstruction of non load-bearing defects of the skull and facial bones (Kuttenberger and Hardt, J. CranioMaxfac. Surg., 2001; Schipper et al., Eur. Arch. Otorhinolaryngol., 2004). The mesh provides a stable, permanent, biocompatible reconstruction which is well tolerated, even when in direct contact with paranasal sinuses.

Titanium mesh is generally shaped free-hand by traditional manual forming and manipulation, or pressworking with a cavity and punch. Unfortunately, accurate restoration of missing anatomy is often difficult, and can be compromised by problems associated with forming a stable molded implant and correctly positioning the implant. This is particularly true when defects are large, involve complex contours or exist in limited access anatomical sites.

SUMMARY

Embodiments provided herein including methods and apparatus for forming a patient-specific surgical implant based on mold system. The apparatus comprises a forming tool and a mold that may be generated using imaging and processing techniques and rapid prototyping methods. The mold apparatus includes at least two non-adjacent surface features for securing an implant forming material (such as a titanium mesh) during the forming process, enabling the implant forming material to be stretched beyond its elastic and thus permanently deformed with the correct patient-specific curvature. The implant may include one or more anatomic surface features for guidance and registration when transferring the implant to a patient.

Accordingly, in one embodiment, there is provided an apparatus for shaping an implant forming material into a surgical implant for correcting a defect in a skeletal region, the apparatus comprising: a mold comprising a defect-free surface profile of the skeletal region; and; a forming tool having a negative surface profile relative to the mold, such that the implant forming material is shaped into the surgical implant when the implant forming material is compressed between the mold and the forming tool; wherein at least one of the mold and the forming tool comprise two or more non-adjacent surface features; and wherein the surface features are configured to locally secure the implant forming material between the mold and the forming tool such that the implant forming material is permanently deformed under application of suitable pressure.

In another embodiment, there is provided an apparatus for shaping an implant forming material into a surgical implant for correcting a defect in a skeletal region, wherein the implant forming material supports lateral fluid flow when the implant forming material is compressed between two surfaces, the apparatus comprising: a mold comprising a defect-free surface profile of the skeletal region; and; a forming tool having a negative surface profile relative to the mold, such that the implant forming material is shaped into the surgical implant when the implant forming material is compressed between the mold and the forming tool; wherein one of the mold and the forming tool comprises a channel, the channel comprising an external port and an internal port, wherein the internal port is in flow communication with the implant forming material when the implant forming material is compressed between the mold and the forming tool.

In another embodiment, there is provided an apparatus for shaping an implant forming material into a surgical implant for correcting a defect in a skeletal region, the apparatus comprising: a mold comprising a defect-free surface profile of the skeletal region; and; a forming tool having a negative surface profile relative to the mold, such that the implant forming material is shaped into the surgical implant when the implant forming material is compressed between the mold and the forming tool; and a reservoir positioned to immerse the implant forming material in a liquid while the implant forming material is compressed between the mold and the forming tool.

In another embodiment, there is provided a kit for forming a patient-specific surgical implant to correct a defect in a skeletal region, the kit comprising an apparatus as described above; and the implant forming material.

In another embodiment, there is provided a method of fabricating a mold system for shaping an implant forming material into a surgical implant such that the surgical implant has a curvature configured to correct a defect in a skeletal region, the method comprising the steps of: obtaining a digital image of the skeletal region; processing the digital image to obtain a three-dimensional model of the skeletal region; processing the three-dimensional model to obtain a defect-free three-dimensional surgical model of the skeletal region; processing the defect-free three-dimensional surgical model and generating a model of the mold system, wherein the mold system comprises a positive mold and a negative forming tool, such that the implant forming material is shaped into the surgical implant when the implant forming material is compressed between the mold and the forming tool; including two or more non-adjacent surface features in one or more of the mold and the forming tool; and fabricating the mold system; wherein the surface features are selected to locally secure the implant forming material between the mold and the forming tool such that the implant forming material is permanently deformed under application of suitable pressure.

In another embodiment, there is provided a method of generating a surgical implant for correcting a defect in a skeletal region during a surgical procedure, the method comprising the steps of: providing an apparatus as described above; positioning the implant forming material between the mold and the forming tool, wherein the implant forming material has a sufficient spatial extent to contact the surface features; and applying a compressive force to the mold and the forming tool to shape the surgical implant.

In another embodiment, there is provided A method of generating a surgical implant for correcting a defect in a skeletal region during a surgical procedure, the method comprising the steps of: providing an apparatus as described above, positioning the implant forming material between the mold and the forming tool, wherein the implant forming material has a sufficient spatial extent to contact the surface features; and applying a compressive force to the mold and the forming tool to shape the surgical implant.

In another embodiment, there is provided a method of generating a surgical implant for correcting a defect in a skeletal region during a surgical procedure, the method comprising the steps of: providing an apparatus including a mold system that incorporates a reservoir as described above, wherein the implant forming material comprises a polymer; adding liquid to the reservoir, where a temperature of the liquid is suitable for softening the polymer; immersing the implant forming material in the liquid; and applying a compressive force to the mold and the forming tool to shape the surgical implant.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 15(c) shows the implant secured to the patient's skull.

DETAILED DESCRIPTION

Figure 1:
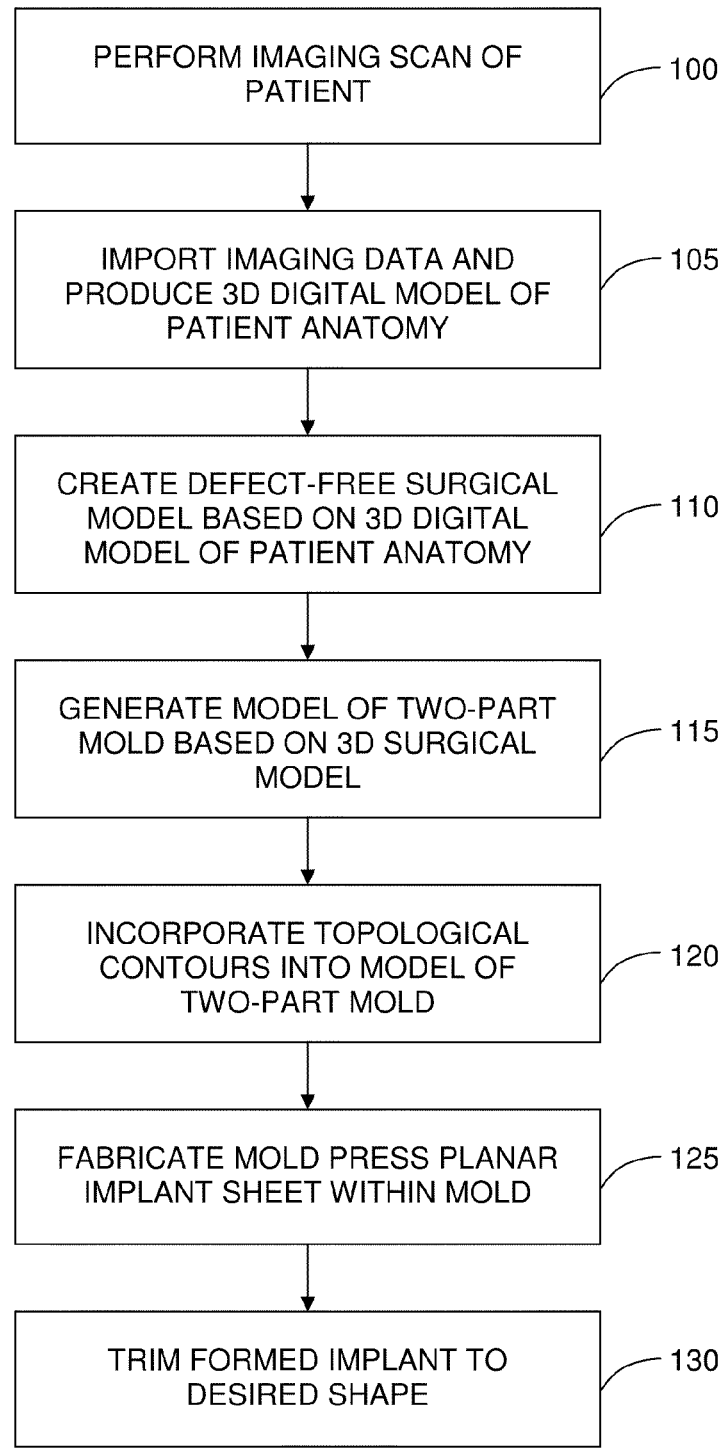
FIG. 1 provides a flow chart illustrating a method of forming an implant.
Figure 2:
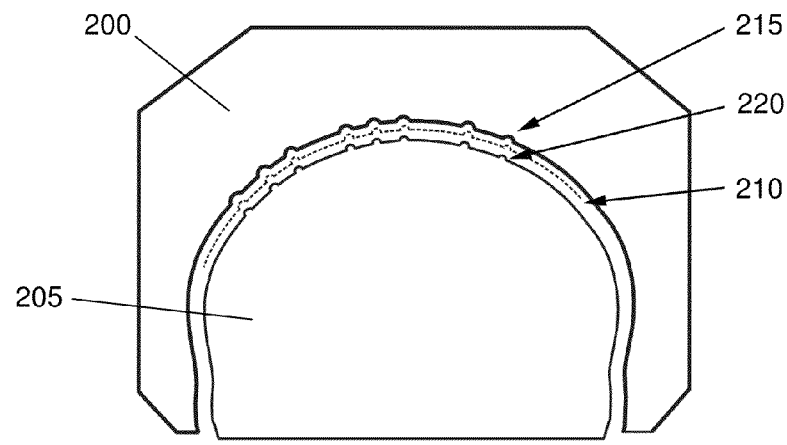
FIG. 2 shows a mold system that incorporates surface features for stretching an implant forming material beyond its elastic limit.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "defect" refers to an anatomical region that requires replacement, covering, or reinforcement, including, but not limited to, holes, fractures, tumors, and deformations. The anatomic region may include, but is not limited to, bone structures such as the skull, jaw, limb, and hip. The exact size, shape and specific location of the defect need not be known prior to surgery.

As used herein, the term "implant forming material" refers to any material that may be formed by presswork to generate a surgical prosthesis for a defect. The resulting implant may be secured by fastening to surrounding bone structures. Suitable implant materials include, but are not limited to, biocompatible metal sheet and mesh structures such as titanium mesh, polymeric sheets such as PMMA, polyethylene, and PEEK, and polymeric resorbable materials such as polylactic-coglycolic acid. The implant forming material may alternatively comprise a hybrid composite polymer-metal structure, for example, a titanium mesh coated with polyethylene such as the MEDPOR® TITAN™ sheets.

As used herein, the term "non-adjacent surface feature" refers to two or more surface features that, when incorporated into a mold system fabricated based on a 3D surgical model, locally secure an implant forming material and produce non-elastic deformation of the implant forming material during a pressworking step in which the implant is formed.

FIG. 1 provides a flow chart illustrating a method of forming a surgical cranial implant according to one embodiment. It is to be understood that embodiments described herein are not limited to cranial defects, and the scope of the embodiments as disclosed herein is intended to encompass a wide range of surgical implants that involve the use of pressworking.

In step 100, a digital imaging system, such as a CT, MRI, or surface scanner, is used to obtain a imaging data pertaining to the patient's cranial anatomy. The imaging step provides anatomical data both within and beyond the region associated with a defect (or an anticipated defect). The imaging data is then imported in step 105 into a standard image format, such as the Mimics™ software platform (Materialise, Belgium). This enables the creation of a 3D model of the patient anatomy. The model may be created using known techniques, such as using the steps of thresholding, region growing and manual editing. Automatic thresholding may be performed to achieve a first approximation of the bony surfaces of the skull, followed by manual editing to obtain a refined model. Haptic modeling, for example using a modeling software platform such as the PHANTOM™ Desktop Haptic Device, may be used to further refine the model.

Having obtained a digital 3D representation of the patient anatomy in step 105, a 3D surgical model is produced in step 110. For example, the 3D surgical model may be produced using a 3D model editing software package such as Magics™ software package (Materialise, Belgium). The 3D surgical model provides a defect-free representation of the patient anatomy, and can be produced by any one of many known techniques. For example, the mirroring technique may be employed, where the non-defective half of the skull is isolated, copied, and integrated to form a new defect-free representation using a subtraction step. Alternatively, the matching technique may be employed, where digital anatomical data from reference subjects is searched to obtain defect-free data that provides a suitable match with the patient anatomy.

Subsequently, in step 115, the 3D surgical model is used to produce a digital model of a two-part mold system including a positive mold and a negative forming tool. The digital data from the 3D surgical model is provided to a suitable software platform (such as the software package Surfacer™) for designing the mold and forming tool of the system. This enables the mold system to be designed stereolithographically. The device consists of a positive and a negative form, in which the positive form (i.e. punch or mold) corresponds to the patient's anatomy (for example, a representation of the skull or facial bones). The negative form (i.e. forming tool) provides a matching surface adjusted to accommodate the thickness of the desired mesh. The mold and forming tool may be offset by an appropriate thickness to accommodate the thickness of the implant forming material. For example, in the case of a titanium mesh plate with a thickness of 0.5 mm, the profile of the mold is offset by 0.5 mm.

A final step in the generation of a model of the two-part mold is the assessment of the model for sufficient surface features, and the optional modification of the model for the inclusion of additional artificial surface features beyond the defect region, as shown in step 120. When incorporated into a mold system that includes a mold and forming tool, non-adjacent surface features that are beyond the defect region provide significant benefits to the process of forming and maintaining the curvature of the implant. In particular, provided that two or more surface features are suitably positioned outside of the defect region and have a sufficient radius of curvature, the surface features will cause implant fixation during the forming step. This allows the mold to frictionally contact the implant forming material at two or more non-adjacent locations, thereby enabling the stretching of the implant forming material during the pressworking process in which the curvature of the mold is transferred to that of the implant.

This key advantage of frictional and static contact between the mold and forming tool and the implant forming material enables the mold and forming tool to stretch the implant forming material beyond its elastic limit during the forming process, which overcomes the elastic memory effect and generates a permanent curvature in the implant. The non-elastic deformation of the implant during the forming process therefore avoids problems associated with elastic or memory shape relaxation, which can cause a formed implant to relax to an incorrect surface profile.

Surface features may be anatomic or artificial. Non-limiting examples of anatomical surface features include rims such as the orbital rim, ridges such as the brow ridges, zygomatic processes, maxillary buttresses, and the margin of the mandible. Artificial contours may comprise any shape that provides a suitable frictional fixing of the implant forming material during the forming process.

The two or more non-adjacent surface features are incorporated outside of the defect region and positioned to cause the stretching of the implant forming material across the defect region during a pressworking step. In some cases, there may already be two adjacent anatomical surface features, such as those associated with the orbital rim. However, in order to provide sufficiently opposing forces for stretching of the implant forming material over the defect region, at least one additional surface feature should be present in a non-adjacent location. For example, if the defect region is on the top of the skull and the mold already includes the brow ridges, an additional non-adjacent artificial surface feature may be located near the back of the skull. The inclusion of the additional surface feature in a non-adjacent location enables the stretching of the implant forming material over the defect region, where the matching of the curvature to the patient anatomy is most critical.

After having ensured the presence of two or more non-adjacent surface features, the model of the two-part mold may then be utilized to fabricate the mold for forming the implant in step 125. The negative forming tool may consist of one or more pieces as appropriate for optimal mesh bending. In one embodiment, a forming liner made from a deformable material is used in conjunction with the mold. The liner allows for variable depth to compensate for variations in thickness of the implant forming material and to ensure that forming pressure is evenly distributed.

Having produced the two-part molded system, the implant forming material may be pressed within the mold and forming tool to produce an implant having the desired surface curvature. Centrifugal tension in combination with a compressive force applied to a planar mesh or other implant forming material allows permanent deformation into a 3D shape. The specific configuration of this 3D shape is dictated by the two-part mold. As noted above, the provision of the non-adjacent surface features enables the stretching of the implant forming material beyond its elastic limit during the presswork step, thereby providing a permanently shaped implant with the correct curvature. The implant forming material used in this step has a spatial extent that is larger that the defection region and extends to the surface features. The larger spatial extent of the implant forming material is also useful in providing sufficient area for the fixation of the implant to adjacent patient tissue such as bone. Compression of the mold and forming tool may be manual or by a mechanical press. The mold components may further comprise an elastic surface for improved stabilization and bending of the implant forming material.

Figure 14:
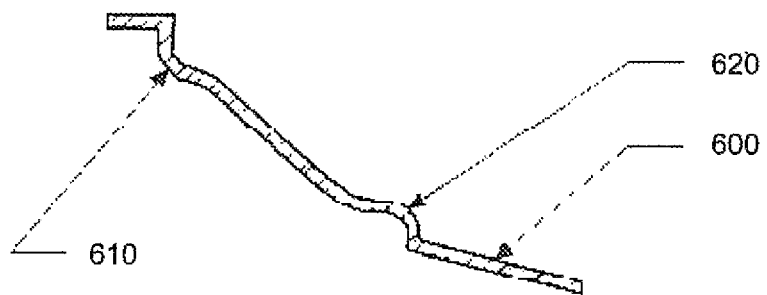
FIG. 14 shows (a) an example of a cross-section of a formed mesh indicating artificial and anatomic contours and (b) an illustration the mesh following removal of the excess mesh leaving a conforming mesh to the anatomy.
Figure 14:
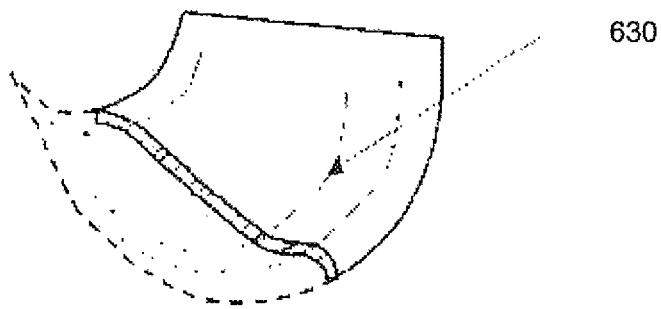

In a final step shown at 130, the implant may be trimmed to a desired shape. The trimming of the implant may be performed prior to transferring the implant to the patient, or after having correctly registered and/or fixed the implant into the patient (optionally after receiving, intra-operatively, information regarding a desired size of the implant). In another embodiment, the mesh may be initially trimmed to a size that includes the surface features, positioned, and then further trimmed to a final size. An example of a formed implant is shown in FIG. 14 (*a*), which provides an example of a cross-section of a formed mesh indicating artificial (600 and 610) and anatomic 620 features. FIG. 14 (*b*) shows an illustration the mesh following removal of the excess mesh leaving a conforming mesh to the anatomy, wherein the contour 630 is characteristic of the curvature describing the missing anatomy in a defect, such that the formed implant will confirm to the adjacent existing anatomy. The lower portion shows an ¾ view of the top piece after trimming away the excess material, including the artificial contours.

In one embodiment, anatomical surface features may be employed to aid in the registration of the implant. The use of anatomical surface features for inter-operative guidance and registration enables the correct placement of the implant onto the patient anatomy, without having to pre-form the implant to a specific spatial size. Specifically, the anatomical surface features allow the implant to be placed upon the patient using a lock-and-key fitting approach.

Figure 22:
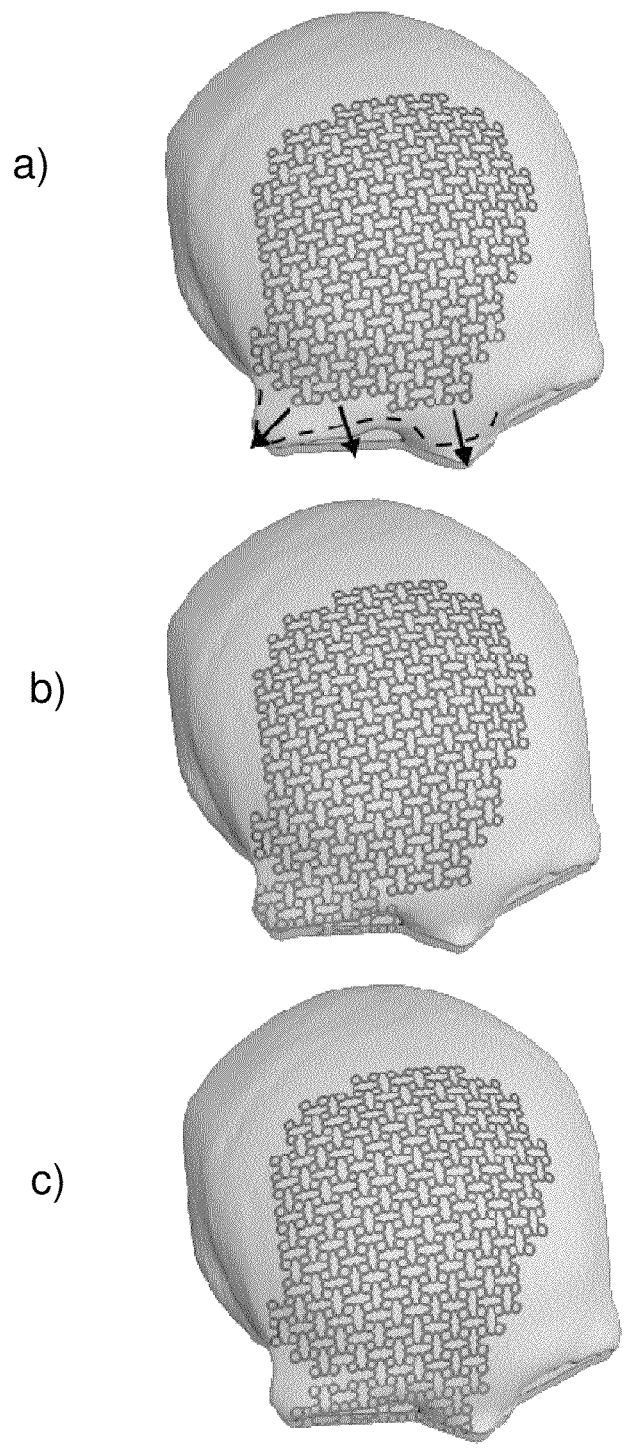
FIG. 22 shows an illustration of a mesh that is (a) formed on a mold near an anatomical feature and (b-c) extended to overlap a portion of the anatomical feature for registration.

In one embodiment, the mold and forming tool are provided as a kit that optionally includes the implant forming material. The mold and forming tool may be pre-sterilized. The mold system and a suitable implant forming material may then be used in a pre-operative or inter-operative setting to produce formed implant that has a large spatial extent. The implant forming material may include a spatial area that extends to at least one anatomical surface feature outside of the defect zone. This allows for the accurate guidance and registration of the implant during a surgical procedure. If the anatomical contour exists well beyond the defect region, the implant forming material may include a tabbed structure to enable accurate placement with the minimum implant forming material. An example of such an embodiment is illustrated in FIG. 22. In FIG. 22(*a*), a mesh is show that is placed near an orbital anatomical feature, and the arrows indicate the direction in which the mesh may alternatively be extended for registration purposes. FIGS. 22 (*b*) and (*c*) show two different example implementations in which the mesh is extended and registered with the anatomical features.

The mold may also include non-topological surface anatomic features that are clearly visible intraoperatively for indirect verification of registration. These include, but are not limited to, cranial suture lines and muscle attachments.

A guide piece may be employed to properly position the implant, where the guide piece contains features that match the underlying patient anatomy for registration and alignment. In one non-limiting example in which the implant has a mesh structure, the guide piece may be an additional mesh structure that is contoured to the patient anatomy and attached to the implant. In another embodiment, the guide piece may be a solid molded structure that may be provided in a sterilized form, such as molded plastic, that is contoured to the patient anatomy and is secured to the implant. The guide piece may be removably attached to the implant for ease in removal after implant registration. In another embodiment, the guide piece may include protuberances or other features that allow the guide piece to be handled with ease when registering the implant to the patient.

Figure 23:
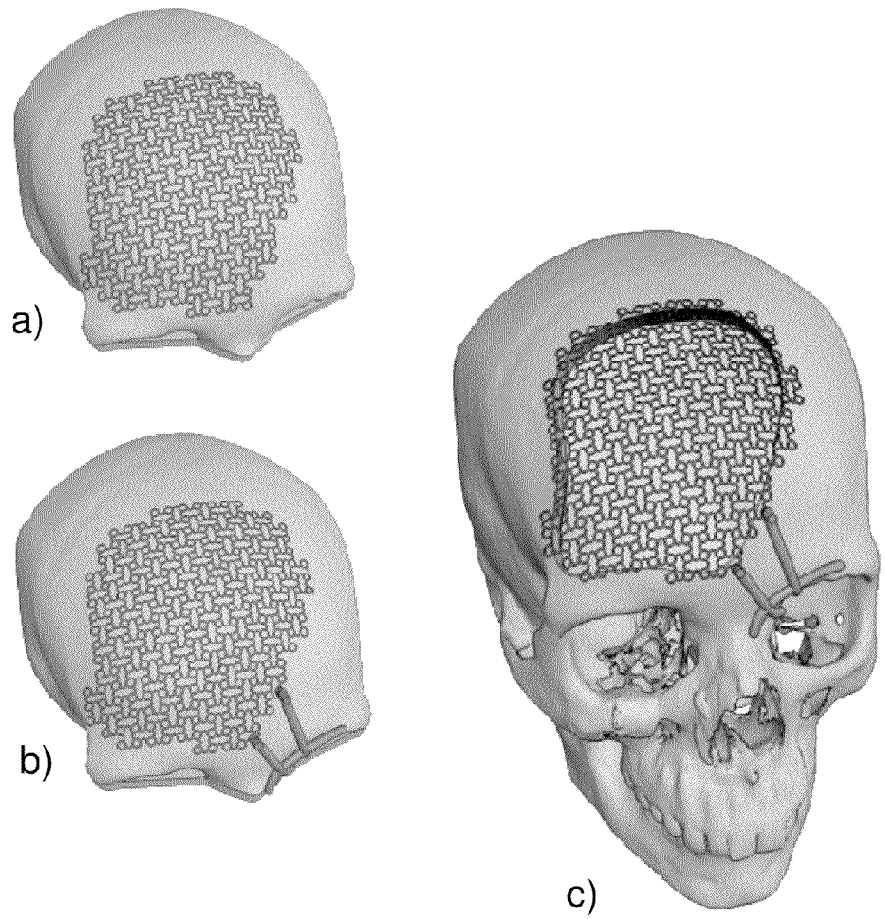
FIG. 23 illustrates an embodiment in which (a) a mesh is shown formed into an implant on a mold, (b) a guide structure is added to the implant for registration, and (c) the implant is indexed to the patient using the guide structure.

FIG. 23 provides an example implementation of an implant that additionally includes a guide piece for registration and indexing. FIG. 23(*a*) shows a mesh that is formed into an implant, where the implant is shown residing on the mold after the forming step. In FIG. 23(*b*), a guide piece is added to the formed implant, and the guide piece is registered to an anatomical feature. The resulting implant and guide piece may then be indexed to the patient, as shown in FIG. 23(*c*), where the guide piece may be conveniently employed for handling and for registration. The guide piece may be removed after the implant is secured to the patient.

The guide piece may be manufactured from a sterilizable material. In one example, the guide piece is formed from the same material as the mold system. The guide piece may alternatively be formed from another other suitable material, such as plastic or another piece of the implant forming material (e.g. mesh). In another example, one or more metal plates could be used to form an appropriate guide piece. The guide piece is formed with a custom curvature to link to the fiducial anatomy (the orbital rim in this case), with at least one or more extensions to the implant forming material. The guide piece may be held in place against the anatomy by one or more curved sections (for example, the hooks perpendicular to the orbital arch in FIG. 23). In cases where the implant forming material is a mesh, the ends of the guides may be matched with pins or the like to connect and hold the mesh by friction fit.

Figure 3:
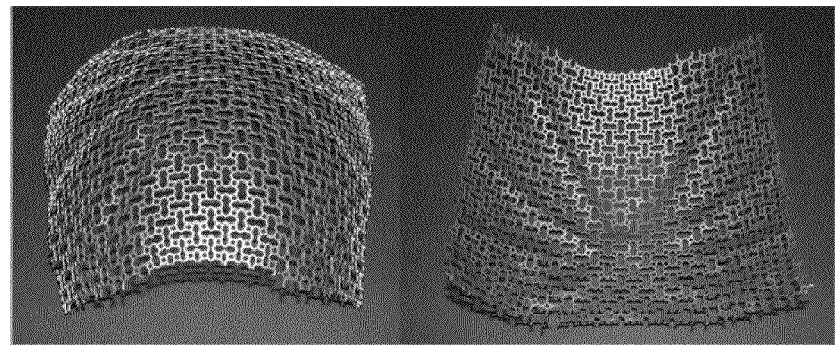
FIG. 3 provides photographs of a mesh implant having additional groove contours.
Figure 4:
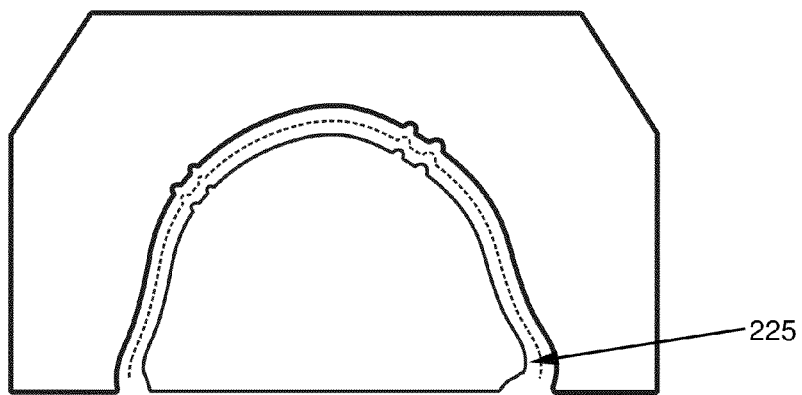
FIG. 4 illustrates a mold incorporating an outer lip for engaging and securing the mold forming material.

FIGS. 3 to 5 illustrate various non-limiting devices and methods for forming an implant with a mold system incorporating surface features. The mold system includes forming tool 200 and mold 205. Implant forming material 210 is provided between forming tool 200 and mold 205, and is formed into a desired shape under a compressive force. FIG.

3 shows one embodiment in which multiple surface features are incorporated into the mold system. For each concave surface feature 215 in the forming tool, there exists a corresponding and mating convex surface feature 220 in the mold piece. The presence of the surface features cause the implant forming material to be stretched and deformed during the pressworking step, thereby retaining the shape of the mold. In other example embodiments, the surface features in one component of the mold system need not have a corresponding feature in the other component. For example, a liner, such as a rubber liner, may be included that is compressed along with the implant forming material, where the liner accommodates surface features in one mold component.

In one embodiment, artificial contours may be added to cross the defect region in addition to the periphery. For example, FIG. 3 provides an image of a mesh-based implant in which artificial radial contour grooves have been included to assist in the inelastic deformation of the mesh in the central region of the implant. Such artificial contours are designed to specifically introduce small grooves in the mesh shape that induces additional rigidity into the mesh.

In one example implementation, the grooves are positioned to extend the intrinsic mesh strength along directions that are approximately perpendicular to the principal surface curvature, acting as reinforcing spines in the mesh structure. The grooves may be positioned to extend the intrinsic mesh strength along directions that are normal to the mesh surface. For example, the mold may include spines that run along curved surface to provide additional strength to compressive force perpendicular to that surface. In one example, the grooves are shallow with a depth of less than about 2 mm from the main surface. Such a shallow depth acts to prevent cosmetic changes to the desired anatomic shape. Similarly, the groove width may be less than 2 mm, as governed by the mesh link intervals. In another example, two or more grooves may be aligned in intersecting directions to provide rigidity along different directions of the meshes.

Figure 5A:
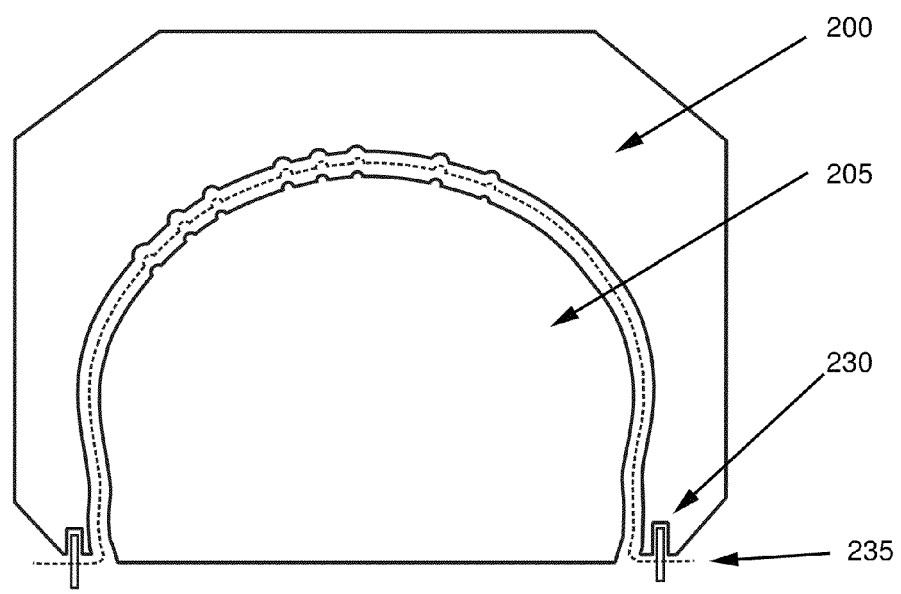
FIGS. 5 (a) and (b) illustrate mold systems in which pins are used to secure a mesh for forming an implant.
Figure 5B:
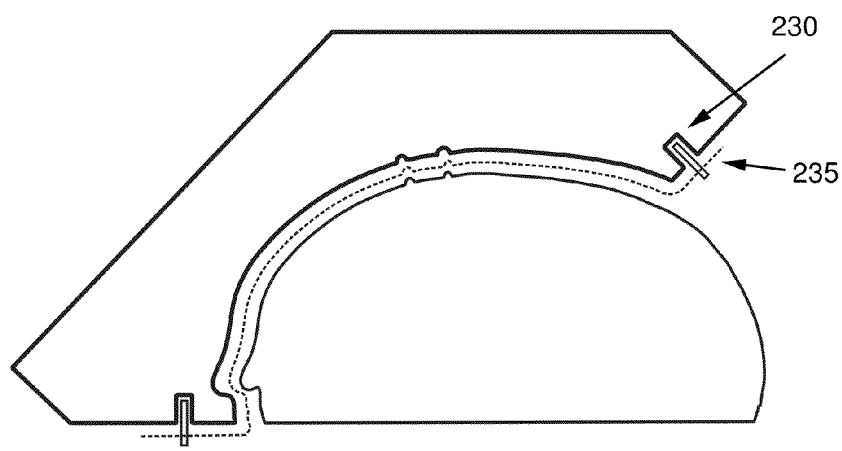

FIG. 4 provides an embodiment in which the implant forming material extends to the lower region of the mold, where it is clamped at 225 between mating beveled surfaces in the forming tool and mold pieces on either sides of the mold. FIGS. 5(a) and 5(b) illustrate embodiments in which the implant forming material includes a mesh, and where clamping pins 230 on either sides of one of the mold components are employed to secure and stretch the mesh. As shown, the pins are may be incorporated at beyond a corner at 90 degrees relative to the primary forming surface, resulting in a flat section of the implant forming material 235 that is secured by the corner and the pin.

According to different example implementations, the pins may be a solid extension of the mold material or a separate insert. For example, FIG. 5 illustrates an embodiment of the pin shape that is compatible with a particular mesh design. The pins may have different cross-sections and placement to be compatible with the mesh shape. The pins can fit into the holes designed for surgical fixation screws or in the interspace created by the mesh links. It is to be understood that the illustrated embodiment involving pins is merely one example of a surface projection suitable for engaging and retaining a mesh-based implant forming material.

Although the artificial surface features shown in FIGS. 3 to 5 are shown as multiple divots with multiple point-like projections, it is to be understood that a wide variety of artificial surface features are compatible with the present disclosure, provided that they have sufficient curvature to secure the implant forming material during compression. For example, an edge or lip may be used, in which a cusp is provided in the mold, over which the implant forming material can be folded to initiate fixation. Once pressed, the sharp cusp acts to hold the implant forming material in place as it is deformed. Alternatively, a groove may be incorporated into the mold, where the groove comprises an indentation and matching ridge. The ridge is adjusted to accommodate the thickness of the implant forming material within the groove. The groove may be a semicircular indentation with edges having a curvature sufficient to induce fixation and deformation. In another non-limiting embodiment, the artificial surface feature may be an interdigitated groove comprising a set of teeth arranged in a row to induce even greater fixation and stretching than the aforementioned smooth groove. Furthermore, as noted in FIGS. 5 and 6, pins matched to the hole size/spacing of a mesh may be employed to achieve rigid fixation.

Figure 6A:
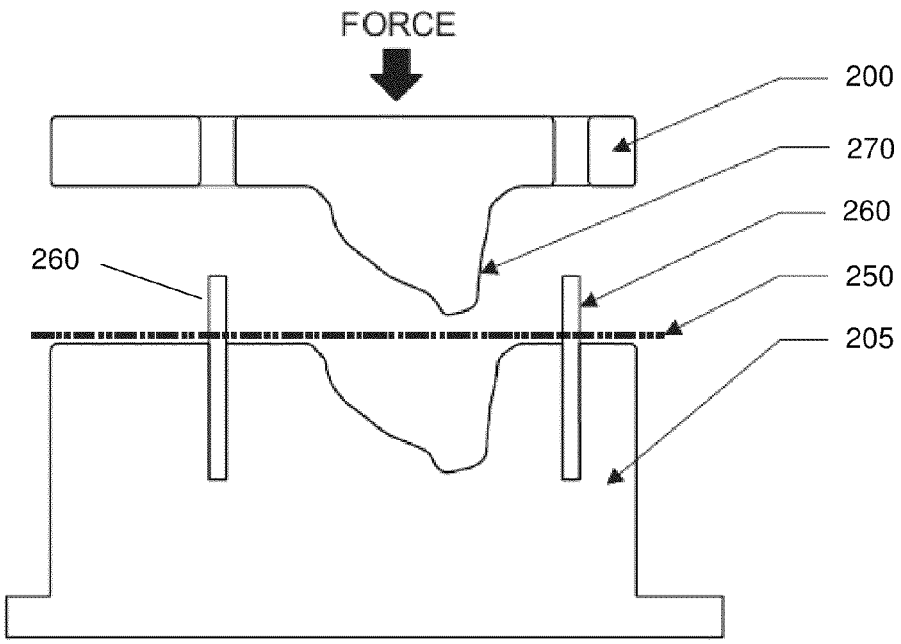
FIG. 6 illustrates (a) a mold system including pins for securing a mesh during compression, (b) an overhead view of the mesh showing the retaining pins, (c) the compressed mesh, (d) the resulting formed implant, and (e) the formed implant trimmed to a desired size.

Referring now to FIGS. 6(a)-(d), an example implementation of a mold system incorporating pins is provided, where the implant forming material is a mesh. FIG. 6(a) shows a two-part mold system including forming tool 200 and mold 205. Mesh 250 is pressed between forming tool 205 and mold 205, and secured in place during the application of a compressive force by pins 260. Forming tool 200 includes a surface profile 270 that is contoured to form a desired implant shape. Surface profile 270 (and a matching inverse profile in mold 205) may include anatomical or artificial surface features.

Figure 6B:
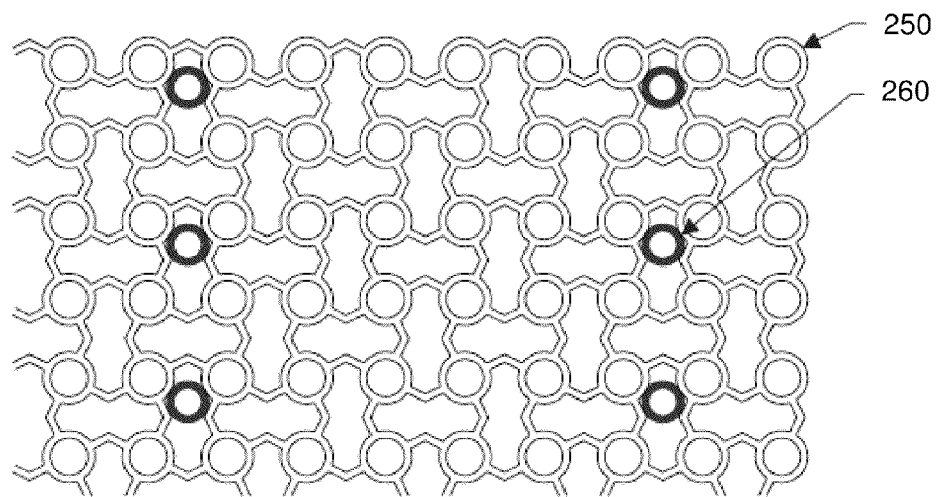
Figure 7:
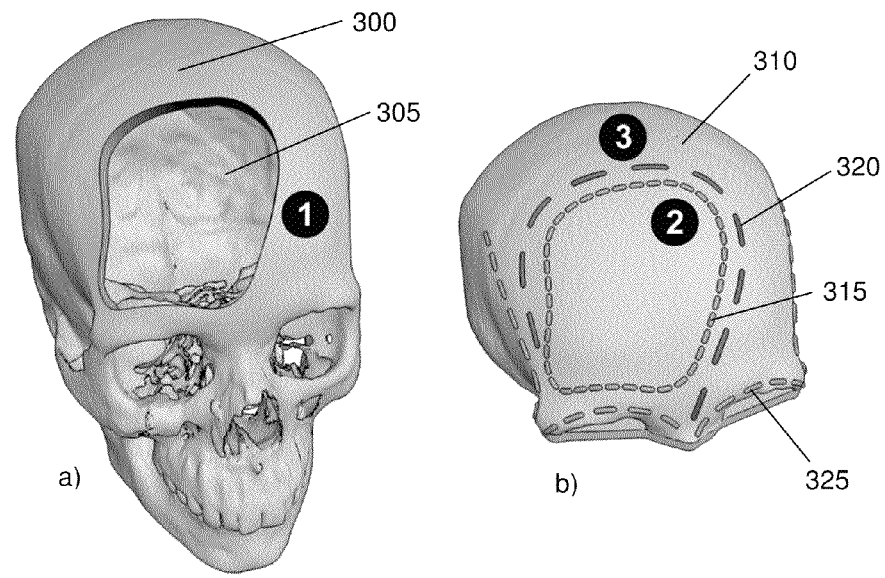
FIG. 7 illustrates (a) a model of a patient's skull showing the planned surgical site and (b) the extent of the implant and planned surface features.
Figure 8:
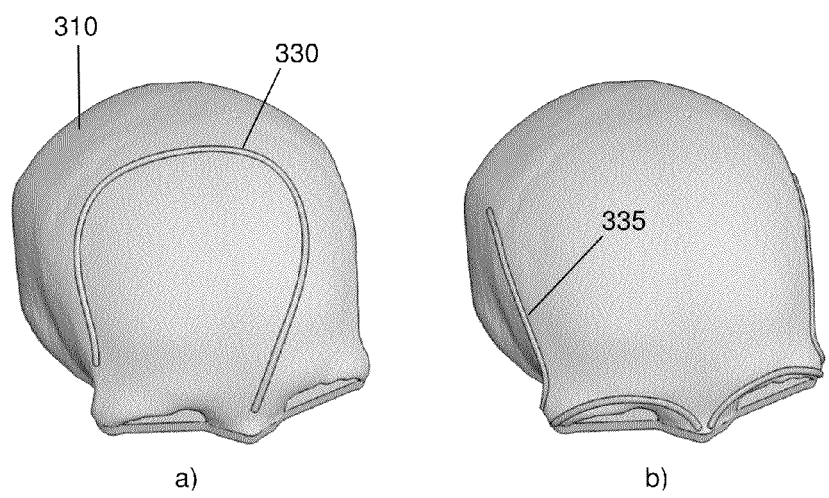
FIG. 8 shows (a) the boundary of artificial surface features and (b) anatomical forming contours.

FIG. 6(b) shows a top view of mesh 250 after it is secured onto mold 205, but prior to the forming step. In the example embodiment shown, mesh 250 is supported and secured by 6 pins 260, which fix portions of the mesh in place during the forming step and assist in producing inelastic deformation of mesh 250. The pressed mesh 255 is shown in FIG. 6(c), which takes the shape of surface profile 270 while being secured by pins 260. The formed mesh 255 is shown after removal from the mold system in FIG. 6(d), which may be subsequently trimmed to provide implant 258, as shown in FIG. 6(e).

Although the example embodiments shown in FIGS. 4 to 6 illustrate clamping or pinning structures at more than one position, it is to be understood that the mold system may include any combination of two or more non-adjacent implant deforming features, where the implant deforming features may include clamping features, pinning features, and topological features.

FIGS. 7-10 further illustrate embodiments in which artificial surface features are employed to secure the implant forming material during the forming step. Referring to FIG. 7(a), a model of a patient skull 300 is shown in which a defect 305 is present. As discussed above, such a model can be obtained using imaging and subsequent image data processing methods. FIG. 7(b) shows a defect-free mold 310 marked with planned locations of the extent of the defect 315, the boundary of an artificial surface feature 320 around and outside of the defect region, and the boundary of an anatomical surface feature 325.

FIG. 8(a) illustrates the mold 310 augmented with an artificial surface feature comprising ridge 330. The ridge, placed outside of the defect region 315, enables the implant forming material to be frictionally secured and stretched during the forming step.

While the mold 310 includes an anatomical surface feature 325, it may be advantageous to augment the anatomical surface feature with an additional artificial surface feature 335, as shown in FIG. 8(b). The additional artificial surface feature provides increased purchase of the mold against the implant forming material and enabling higher strain to be applied to the implant forming material during the application of a compressive force.

Figure 9:
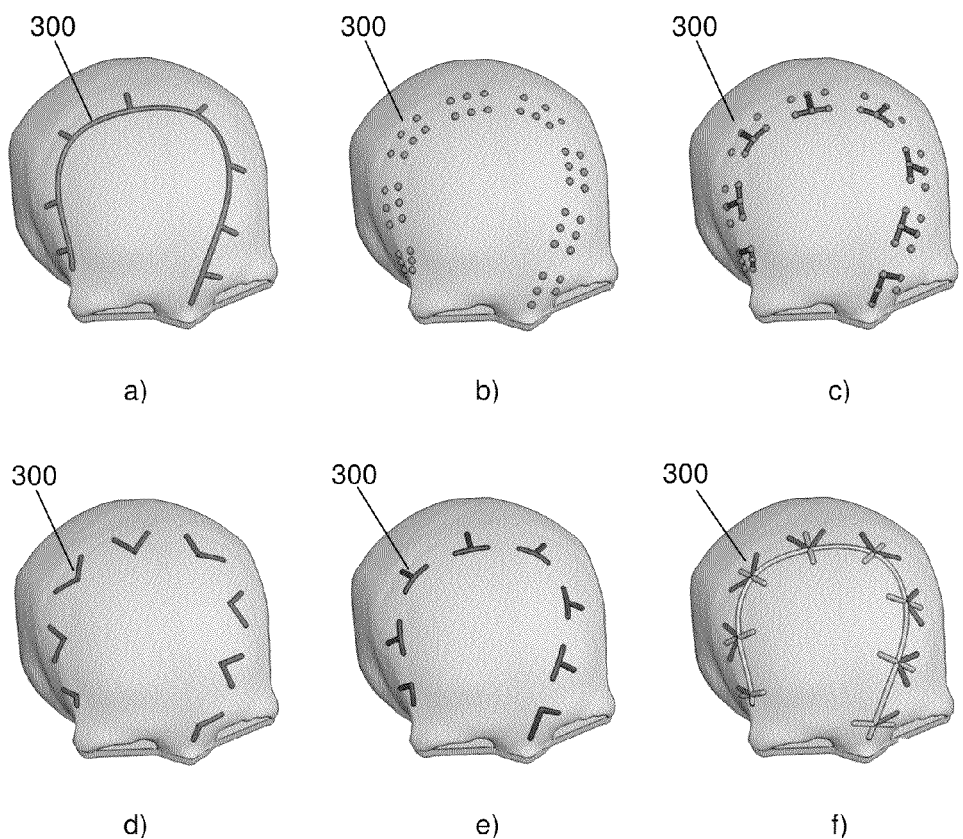
FIGS. 9 (a)-(f) illustrate various types of artificial surface features.

FIGS. 9 (a)-(f) illustrate additional non-limiting variations of artificial surface features that may be incorporated into the mold (and corresponding forming tool). As shown in the Figure, the artificial surface features may include dimple or raised point-like structures, long ridges, short ridges, and combinations thereof. The surface features may be arranged around the perimeter of the defect region in order to provide optimal adhesion and substantially uniform strain. This can be particularly advantageous in avoiding wrinkles and other imperfections in the transferred curvature. The surface features may be formed as an integral part of the mold system, or may be attached to the mold system after initial fabrication of the forming tool and mold.

Figure 10:
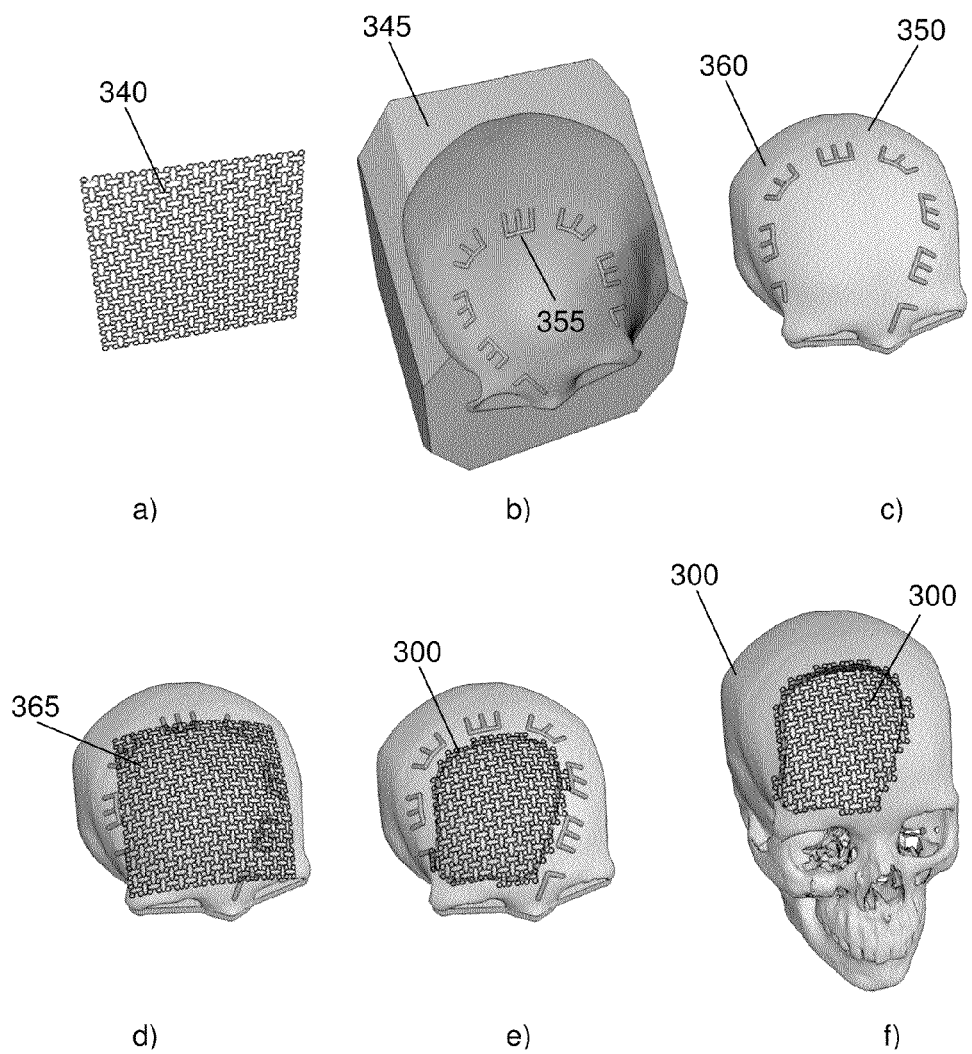
FIG. 10 shows (a) a metal mesh implant forming material, (b) the forming tool of the two-part system, (c) the mold, (d) the mesh formed into a 3D shape over the mold after the presswork forming step, (e) the trimmed implant, and (f) the implant transferred to the patient skull.

FIG. 10 illustrates the steps in the forming process using a forming tool and mold incorporating artificial surface features. FIG. 10(a) shows a metal mesh 340 that is molded to form the final implant and FIGS. 10(b) and (c) show the forming tool 345, mold 350, and artificial surface features 355 and 360. The forming tool 345 and mold 350 are employed to compress and inelastically stretch mesh 340, thereby producing contoured mesh 365 as shown in FIG. 10(d). FIGS. 10(e) and 10(f) show the mesh trimmed to the appropriate size and transferred to the patient.

Although the preceding embodiments have been illustrated involving the use of mesh structures for the implant forming material, it is to be understood that a wide range of implant forming materials may be employed without departing from the scope of the present disclosure.

In one embodiment, the mold system may be configured for the formation of an implant based on an implant forming material that may be formed under compression after an initial thermal softening step. An example of such an implant forming material is a composite mesh. Composite meshes typically consist of a metallic mesh substrate coated with a polymer. An example of a suitable polymer is porous polyethylene. Because of the rigidity of the composite mesh at room temperature, the mesh does not bend well without added heat. Heating softens the polymer coating and allows it to deform without cracking.

Figure 11:
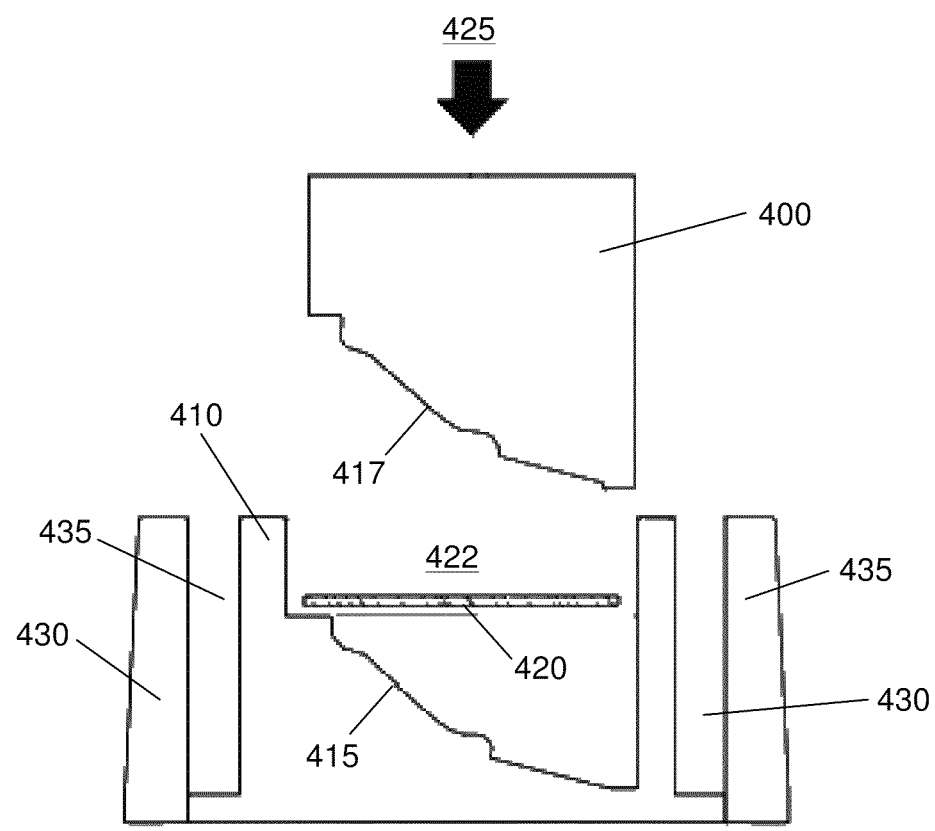
FIG. 11 shows a mold system including a liquid bath for immersing the implant in a fluid prior to or after compression.

FIG. 11 illustrates an example implementation of a mold system that enables immersion of the implant forming material within a cooling or heating liquid to heat and/or chill the mesh. The mold system includes forming tool 400 and mold 410, which include corresponding negative and positive surface profiles 415 and 417, respectively, for shaping the implant forming material under a compressive force. Implant forming material 420 (such as a composite mesh) is placed within upper recess 422 of mold 410. Liquid with a temperature suitable for softening implant forming material 420 is introduced into mold 410 such that the liquid immerses implant forming material 420. The liquid may be a sterile liquid, such as sterilized water.

After the liquid has contacted and softened implant forming material 420, implant forming material 420 is compressed between forming tool 400 and mold 410 under application of compressive force 425. As forming tool 400 is brought into close proximity to mold 410, liquid residing in and below recess 422 is forced outwards and overflows into reservoir 435 of outer housing 430.

The liquid may be heated to a suitable temperature prior to its introduction into mold 410. Mold 410 may include a heat source for heating the liquid. Suitable heating sources include resistive heating elements and an external closed-loop liquid heat exchanger that interfaces with internal flow channels within mold 410. Additionally, a thermal sensor may be included in mold 410 to provide a measurement suitable for maintaining a desired liquid temperature (for example, under a feedback control scheme using an external controller or processor).

Once compressed, the formed implant may be immersed in a cooling liquid, such as chilled water, to harden or 'freeze' the implant to maintain the deformed shape. This may be performed by removing the formed implant and immersing or otherwise contacting it with cooling liquid, or by contacting the formed implant with the cooling liquid after removing the forming tool, but before removing the formed implant from the mold. The formed implant may subsequently be trimmed to a desired shape before or after affixing it to a skeletal region on a patient.

Referring now to FIG. 12(a), an example implementation of a mold system is shown where forming tool 400 includes fluid channel 440 having an external port 445 and an internal port 447. Heating liquid may be introduced into external port 445, where it flows through forming tool 400 and emerges from internal port 447 to contact implant forming material 420 (internal port 447 is in flow communication with implant forming material 420 when implant forming material 420 is compressed between forming tool 400 and mold 410. In the embodiment shown, implant forming material 420 may be a mesh or other suitable porous material such that liquid may permeate implant forming material 420 when it is compressed, such that liquid introduced into external port 445 flows through channel 440, emerges from internal port 447 to contact implant forming material 420, and flows through implant forming material 420, thereby heating implant forming material 420.

After having formed the implant, cooling liquid, such as chilled water, may be injected to harden or 'freeze' the formed implant to maintain the deformed shape. For example, as the compression drops, the liquid can flow through the interspace between the formed implant and the mold system components to provide cooling. The formed implant may be extracted and trimmed to a desired size.

In one example implementation, as illustrated in FIG. 12(b), liquid may be introduced into external port 445 under pressure, such that liquid flows through channel 440, emerges from internal port 447 to contact implant forming material 420, and flows through implant forming material 420, and overflows mold 410 into external reservoir 435 of outer housing 430. A flow mechanism may be employed to recirculate the liquid from reservoir 435 to external port 445. Suitable flow mechanisms include automated flow mechanism such as a pump, and manual flow mechanisms such as a syringe.

In one embodiment, liquid may be reheated or cooled before being reintroduced into port 445 under recirculation. By employing a porous implant forming material that exhibits resistance to flow (for example, due to capillary forces within the implant forming material pores or channels), a restoring fluid force is provided that acts to distribute the fluid within the implant forming material. Accordingly, a substantial or complete amount of implant forming material 420 may be effectively heated or cooled by the liquid.

Figure 12:
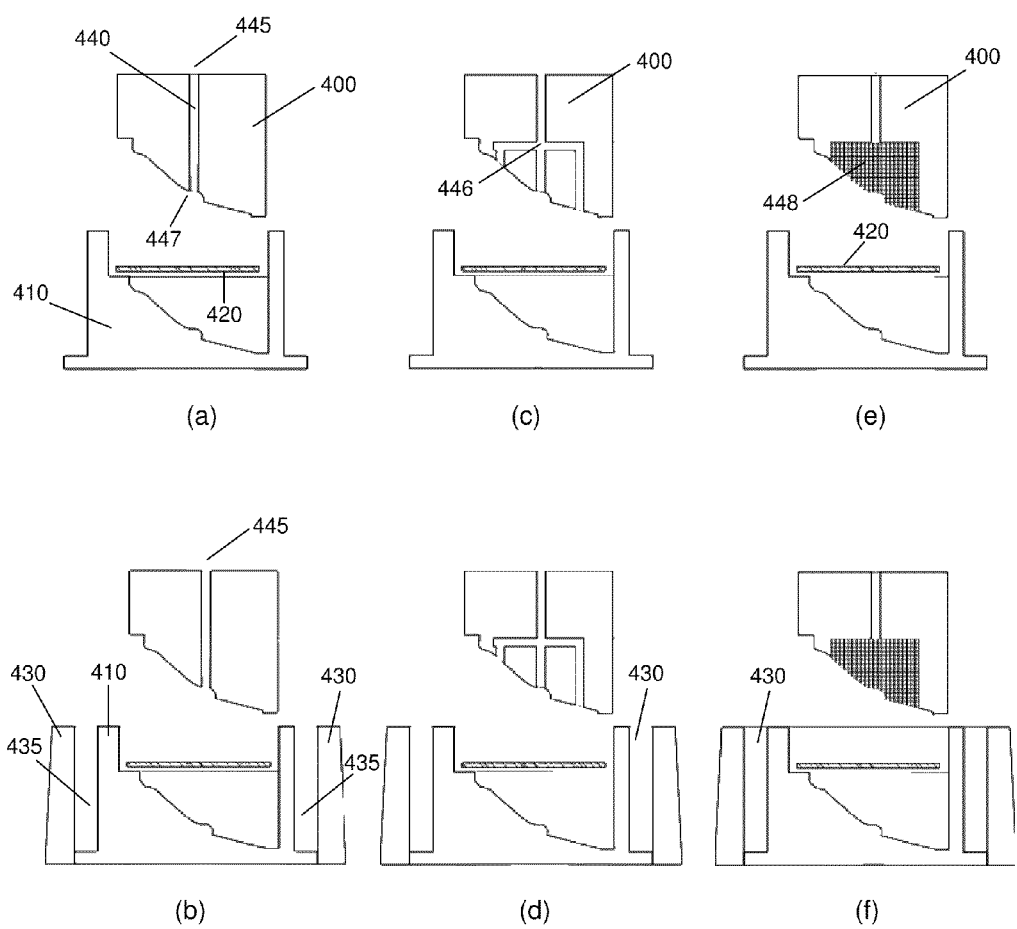
FIG. 12 (a)-(l) illustrates various example embodiments of a mold system for contacting the implant forming material with a liquid before, during or after compression.
Figure 12:
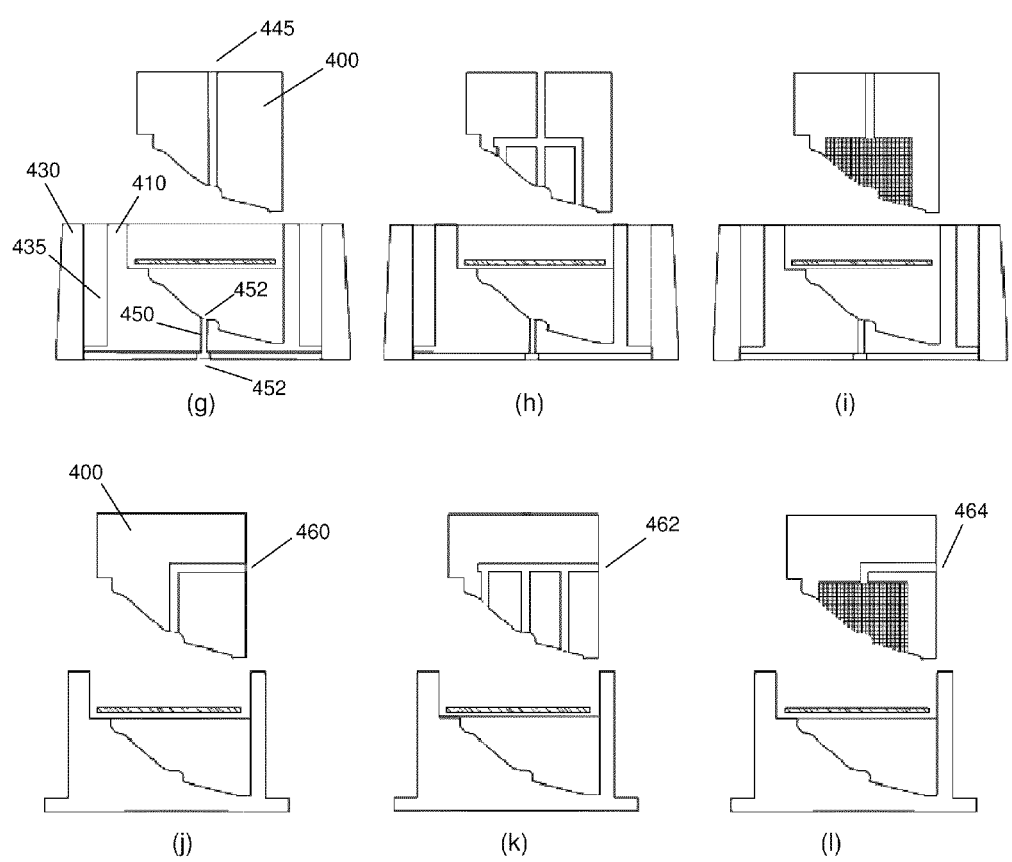

FIGS. 12 (c) and (d) show alternative example embodiments involving a multi-channel structure 446 within forming tool 400, with and without external reservoir 430, respectively. Additional channels 446 may be beneficial in providing more rapid and/or even liquid distribution. FIGS. 12 (e) and (f) show alternative example embodiments involving a porous internal structure 448 within forming tool 400, with and without external reservoir 430, respectively. Porous internal structure may be beneficial in providing a larger thermal mass within forming tool 400, and generating a more even temperature distribution within implant forming material 420.

As shown in FIGS. 12 (g)-(i), one or more additional channels 450 may be provided in mold 410, where additional channel 450 is shown having an additional inlet port 452 in fluid communication with implant forming material 420 when implant forming material is compressed between forming tool 400 and mold 410, and an additional external port 454. Additional external port 454 may be in flow communication with reservoir 435, or with an additional reservoir. As described above, a flow mechanism may be employed to recirculate the liquid from reservoir 435 or from additional external port 454 to external port 445.

FIGS. 12 (j)-(l) illustrate alternative embodiments where external port 460 exits forming tool 400 in a horizontal direction. A horizontal external port exiting mold 410 may also be employed in an alternative embodiment of FIGS. 12 (g)-(i).

While FIG. 12 illustrates selected combinations of fluidic elements, it is to be understood that any or all of the features shown may be combined in a given implementation.

Figure 13:
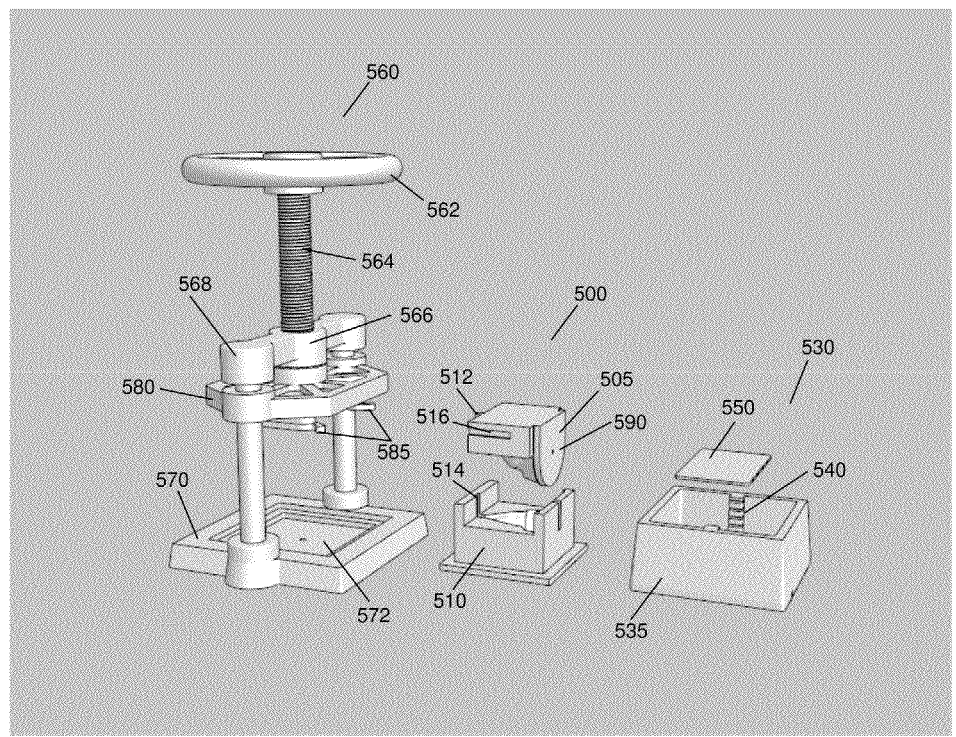
FIG. 13 illustrates an example of a mold system including a mechanical press and a thermal bath.

FIG. 13 illustrates an example implementation of a mold system that includes a two part mold 500, a thermal bath 530, and a mechanical press 560. Two part mold 500 includes forming tool 505 and mold 510. Mold 510 may include a slot 514 or other suitable feature for registering a mating structure 516 in forming tool 505.

Thermal bath 530 includes a housing 535 for receiving and supporting mold 510, such that mold 510 may be filled with a thermal liquid to optionally soften implant forming material 550 prior to compression. In one embodiment, thermal bath 535 includes one or more retaining structures, such as lateral retaining slots 540, for maintaining implant forming material in a submerged position prior to or during the forming process. Additional example retaining structures include hooks and flanges. Accordingly, implant forming material 550 is prevented from experiencing buoyant motion such as floating out of a suitable position prior to or during the forming process.

Mechanical press 560 includes a vise having a rotatable handle 562 connected to a threaded shaft 564 that is received within nut portion 566 of fixture 568. Fixture 568 includes base portion 570 having recess 572 for receiving thermal bath 535. Rotation of rotatable handle 562 causes axial motion of platform 580, which applies a compressive force between forming tool 505 and mold 510 when forming tool 505 and mold 510 are seated in thermal bath 535.

Forming tool may be secured onto a lower portion of platform 580 by fingers 585 that are received within slotted portions 516 of forming tool 505. This enables implant forming material to be optionally heated by a fluid in thermal bath 535 prior to contacting implant forming material 550 between forming tool 505 and mold 510.

It is to be understood that anatomic and/or artificial surface features may be incorporated into the embodiments illustrated in FIGS. 11, 12 and 13.

In one embodiment, the implant forming material (such as a metal mesh, alloy mesh, or a composite polymer-metal mesh), the forming tool, and the mold are sterile and/or sterilizable. In one embodiment, the mold system may be sterilized by disassembling the mold system and sterilizing each component. In an example implementation, a mold system according to the aforementioned embodiments may be provided to form an implant forming material, such as a metal or composite mesh, into a shape that restores the boney surface of the orbital recess. Restoration of a fractured orbital floor is a common surgical task to which custom implants as disclosed herein are suitable. Of particular note is the complex curvature of the orbital floor that is generally a concave surface that accommodates the bulk (globe) of the eye rising to a broad plateau as the orbital recess narrows behind the globe to support the ligaments and central nerve bundle. Current restoration methods and devices generally rely on manually bending flat meshes or highly specialized orbital floor plates. Unfortunately, it is difficult to match both the appropriate depth of concavity of the orbital base and the rising plateau at the distal end of the orbital floor.

Using an implant formed according to the above embodiments, the curvature of the original floor can be restored by creating a mirror of the unaffected orbit. Similarly defects of the roof, lateral and/or medial walls of the orbit, combined defects of two or more contiguous walls of the orbital cavity, can be reconstructed in this fashion.

The orbital forming mold system consists of two parts, one corresponding to the surface of the desired orbit surface and the other the negative of that surface, offset by thickness of the mesh to be bent. Because of the curvature of the orbital rim, this anatomic feature serves as both the registration and fixation surface for inducing inelastic deformation of an implant forming material such as a mesh. The distal portion of the mesh can be bent over a sharp edge to induce tensile deformation under compression, as illustrated in FIG. 5. Generally, the meshes employed for orbital reconstruction are thinner than those used elsewhere in the skull. As a result, the two-piece orbital tool may be used with manual compression. Alternatively, the mold system may be compressed in a mechanical press for added compressive force, for example, as illustrated in FIG. 13.

The following examples are presented to enable those skilled in the art to understand and to practice embodiments of the present disclosure. They should not be considered as a limitation on the scope of the present embodiments, but merely as being illustrative and representative thereof.

EXAMPLES

Example 1

Patient with Post-Infection Frontal Skull Defect

Figure 15:
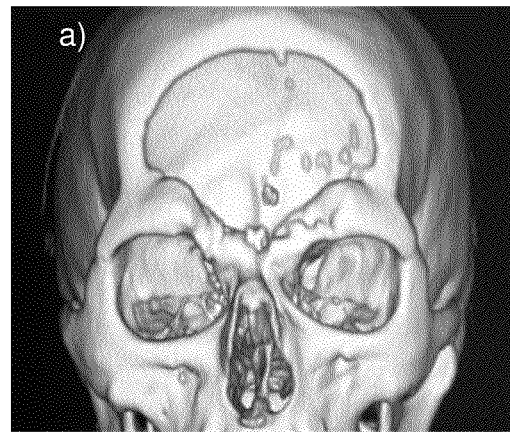
FIG. 15 shows (a) a 3D CT scan of a frontal skull defect prior to surgery, (b) a photograph showing the fabricated mold and forming tool, and (c) the deformed mesh having a curvature conforming to that of the mold.
Figure 15:
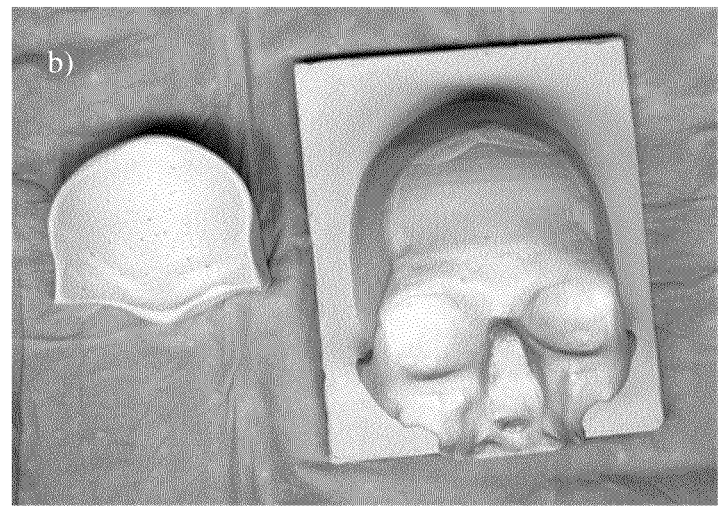
Figure 15:
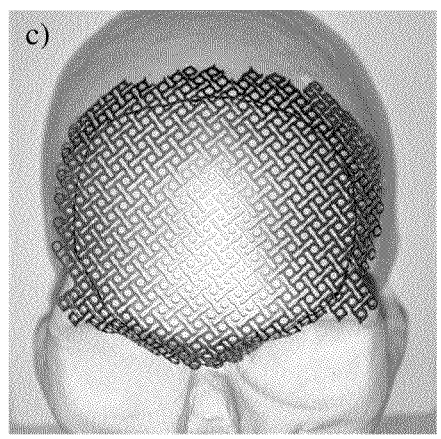

FIG. 15(a) shows a 3D CT scan of a frontal skull defect prior to surgery. Prior to surgery, it was determined that further removal of bone during the surgical procedure may be necessary to obtain clear margins free of infection. The final defect size was therefore not fully determined prior to surgery.

The missing geometry in the forehead was modeled to generate a 3D physical prototype of the desired final skull shape according to aforementioned embodiment. The fabricated mold and forming tool are shown in FIG. 15(b). The mold comprises the virtually reconstructed defect as well as the surrounding key anatomical features. The forming tool (shown on the left) conforms to the mold, and similarly extends to the surrounding key anatomical features, well beyond the defect.

Figure 16:
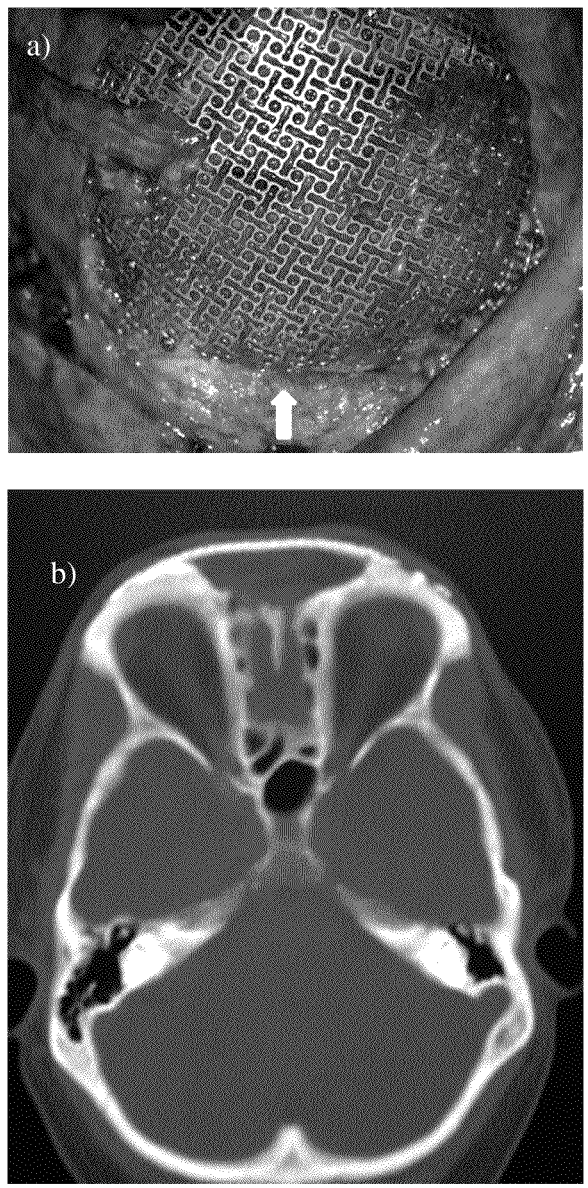
FIG. 16 provides (a) an intra-operative photograph of the mesh secured to the frontal skull and (b) a post operative axial CT cross-section showing formed mesh in place with restoration of the forehead contour.

During the surgical procedure, titanium mesh was shaped between the mold and forming tool. Conforming mesh to anatomical landmarks beyond the defect (in this case the eyebrow ridges and nasal root) ensures accurate spatial orientation and placement of the implant and stretching of the mesh beyond its elastic limit during the forming process. FIG. 16(a) provides an intraoperative photograph of the mesh secured to the frontal skull. Forehead soft tissues have been stripped and reflected downwards to expose the entire frontal skull. The location of the nasal root is indicated by the white arrow. The titanium implant has been fitted to the eyebrow ridge contours and nasal root to ensure optimal positioning in the reconstruction of the defect. and FIG. 16(*b*) provides a post-operative axial CT cross-section showing formed mesh in place with restoration of the forehead contour.

Example 2

Fronto-Orbital Skull Defect, Unknown Size and Shape

Figure 17:
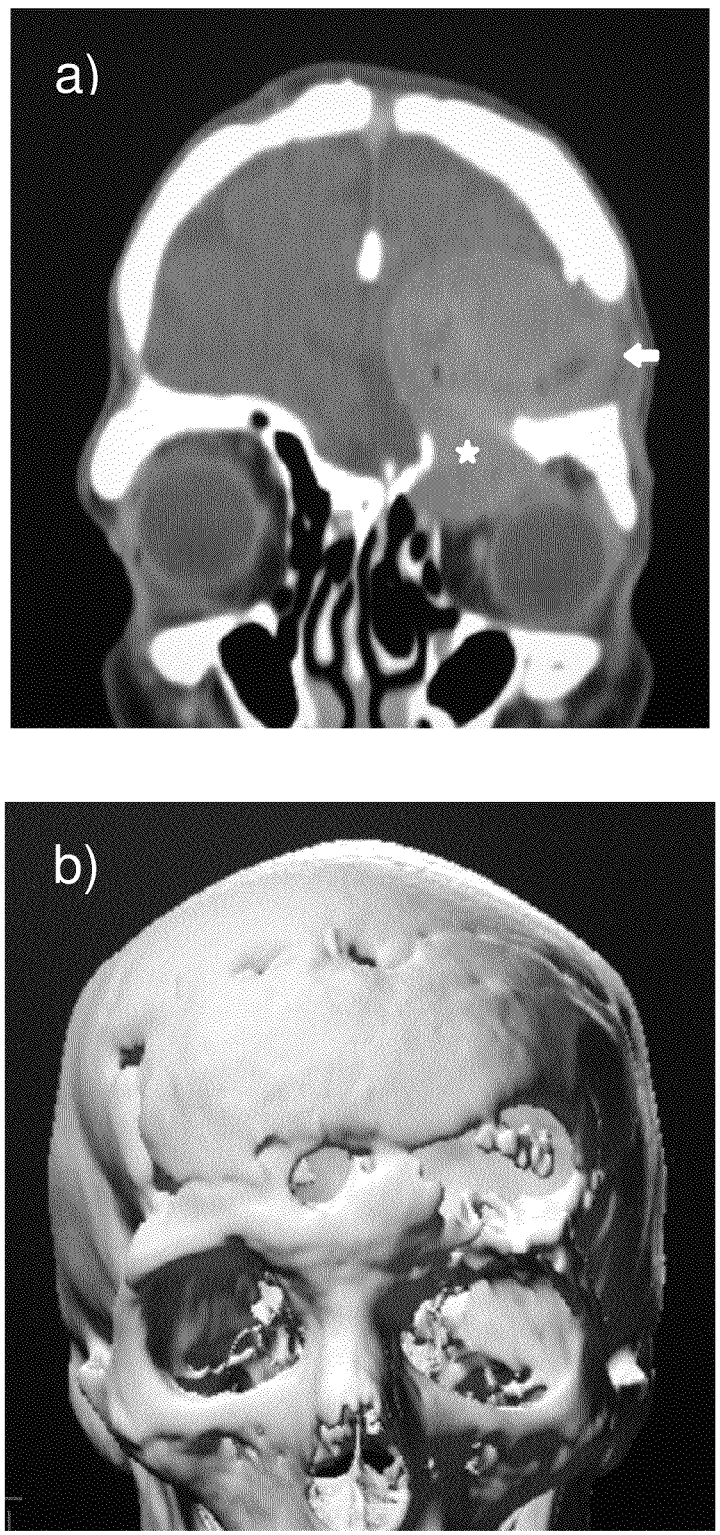
FIG. 17 shows CT image data demonstrating mucocele (mass) eroding through skull from within, and (b) 3D CT showing a defect in the skull, but where further resection at time of surgery will be necessary (the exact defect region is unknown prior to surgery).

FIG. 17(*a*) shows a coronal CT cross-section demonstrating a large left intracranial tumor, which is eroding through bone into the forehead (white arrow), and through the base of the skull into the left orbital cavity (white star). FIG. 17(*b*) is a 3D CT scan in which the size of the skull defect prior to surgery is shown. The defect was expected to be much larger following tumor resection, and accordingly it was not possible to predict the ultimate size and shape of the defect prior to surgery.

Figure 18:
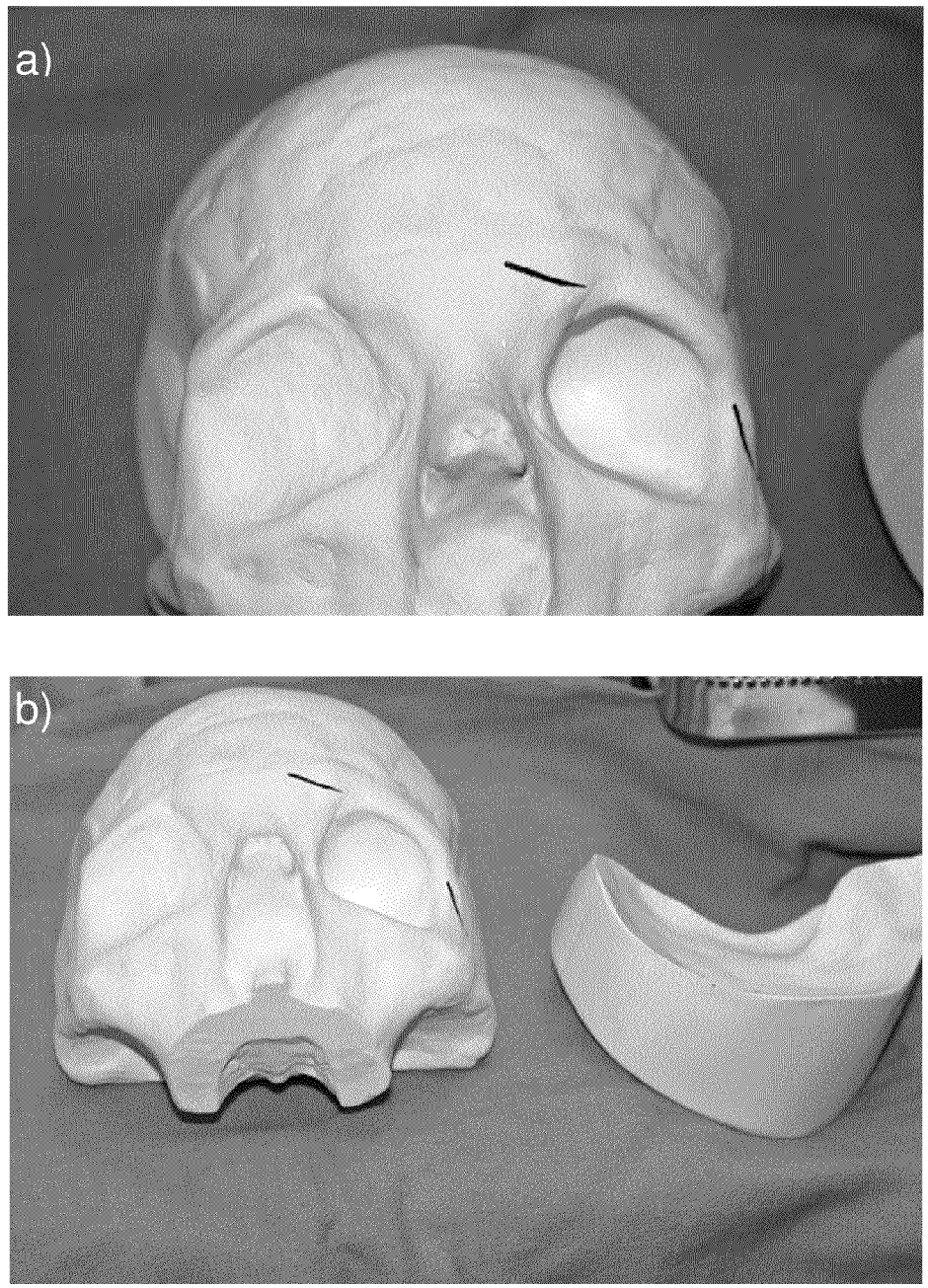
FIG. 18 shows (a) a mold of the patient-specific skull shape, with the defect obliterated and restored to normal shape, and (b) the mold and forming tool of the two-part system.

Virtual modeling of the desired skull and orbital shape in relation to surrounding anatomy was completed to produce a physical prototype of the desired final result. FIG. 18(*a*) and (*b*) show the fabricated mold and forming tool. Bilateral eyebrow ridges, nasal root, orbital cavities, serve as anatomical contours and skeletal references and assist in providing permanent mesh deformation during forming.

Figure 19:
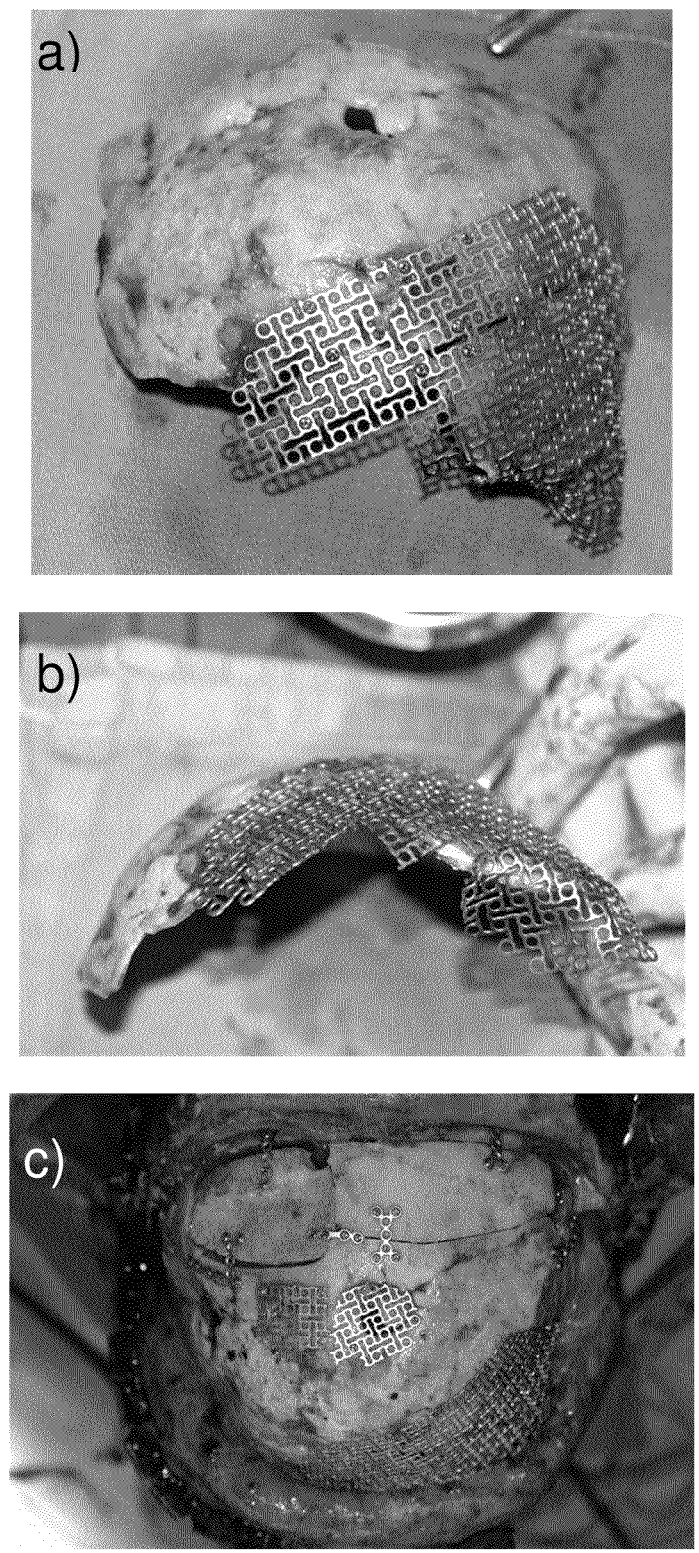
FIGS. 19 (a) and (b) show photographs of the contoured mesh secured to the patient's bone.

The entire frontal bone is shown in FIG. 19(*a*), as seen from the front. The shaped titanium mesh implant restores skeletal continuity, integrity and symmetry to the forehead. FIG. 19(*b*) provides a view from below, where the shaped titanium implant has been conformed around the eyebrow ridge and into the roof of the orbit. The frontal skull viewed from above is shown in FIG. 19(*c*). The root of the nose is at the bottom of the photo. Because the implant extends beyond the margins of the defect to unaltered anatomical reference points, optimal spatial orientation and position are ensured.

Example 3

Orbital Floor Defect

Figure 20:
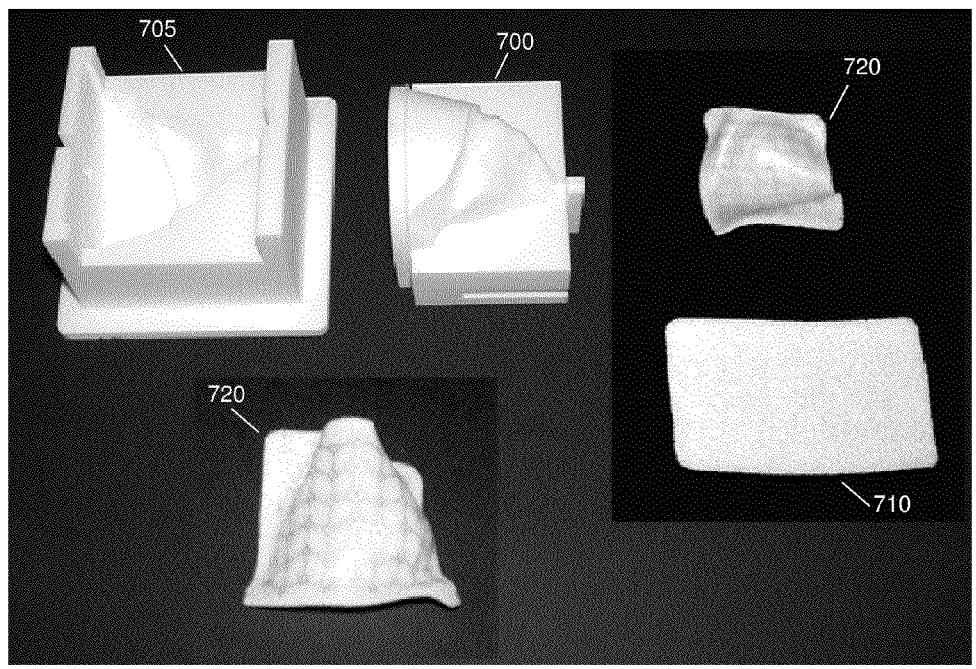
FIG. 20 provides images of an orbital reconstruction mold system and the implant forming material before and after the forming process.

FIG. 20 provides a photograph of a mold system for the repair of an orbital defect using a mesh. The mold system includes forming tool 700 and mold 705, which may be compressed (for example, manually compressed) to form composite mesh 710 into formed surgical implant 720.

The mesh employed in this example was a Medpor® composite mesh, and the implant was formed using the system shown in FIG. 13. The mesh was heated in the hot water bath 535 to soften the mesh prior to compression in the mold system. The water was heated to a near boiling temperature, but water was not boiling when the mesh was implant submerged. The mesh may also or alternatively be separately pre-heated prior to the compression step.

The mesh was mounted in mold 510 and the forming tool 505 was aligned and mounted in mechanical press 560. The mechanical press 560 was closed and more hot water was injected into port 590 as the press was compressed down on the forming tool assembly. The forming tool and mold were fully compressed together to their limits and left in position.

After applying the compressive force, with the composite mesh compressed between the forming tool and the mold, cold water was injected through port 590 in the mold system in order to harden the formed mesh. Alternatively, the entire assembly may be immersed in cold water. Finally, the forming tool and the mesh were separated, and the implant formed from the composite mesh was removed and trimmed to a desired size.

Figure 21:
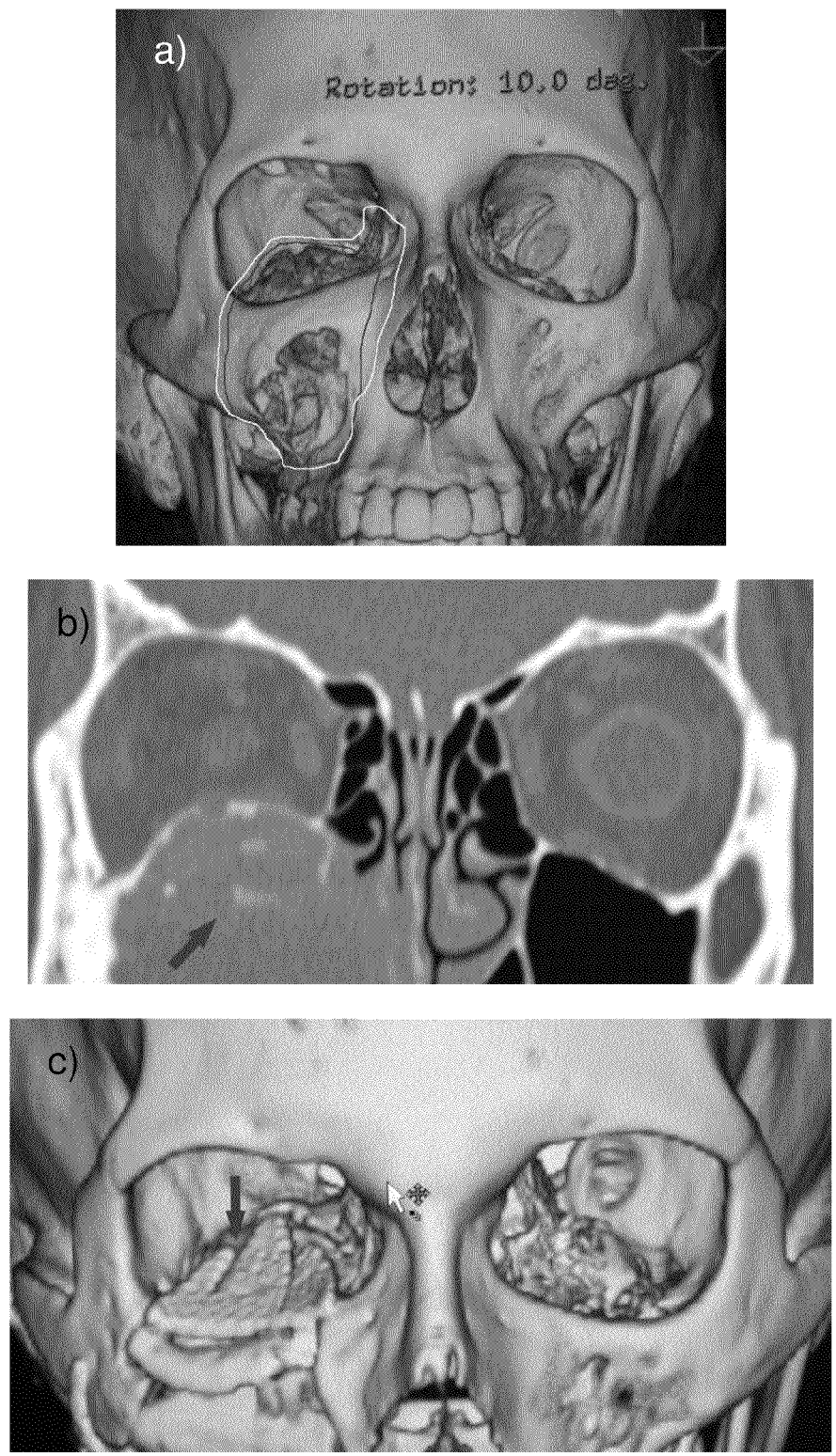
FIG. 21 shows (a) a pre-operative 3D CT scan demonstrating a tumor in the right orbit and maxilla to be resected, where the resection margin is unknown pre-operatively, (b) a post-operative coronal CT scan illustrating the position (marked by arrow) of a mesh that was custom formed, and (c) a post-operative 3D CT scan illustrating the position (marked by arrow) of the custom-formed mesh in three dimensions.

FIG. 21(*a*) demonstrates a tumor in the right orbit and maxilla to be resected, where the resection margin is unknown pre-operatively. In particular, the defect size, shape or location are unknown. FIG. 21(*b*) is a post-operative coronal CT scan illustrating the position (marked by arrow) of a mesh that was custom formed according the methods provided above for restoring orbital continuity and anatomy on coronal cross-section. FIG. 21(*c*) is a post-operative 3D CT scan illustrating the position (marked by arrow) of the custom-formed mesh in three dimensions.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An apparatus for shaping an implant forming material into a surgical implant for correcting a defect in a skeletal region, the implant forming material comprising a solid deformable structure, said apparatus comprising:
a mold comprising a defect-free surface profile of the skeletal region; and
a forming tool having a negative surface profile relative to said mold, such that the implant forming material is shaped into the surgical implant when the implant forming material is compressed between said mold and said forming tool;
wherein at least one of said mold and said forming tool comprise two or more non-adjacent surface features; and
wherein each surface feature is configured to produce fixation of a portion of the implant forming material at a location associated with said each surface feature when the implant forming material is compressed between said mold and said forming tool, such that the implant forming material is stretched between said surface features and permanently deformed beyond its elastic limit under application of suitable pressure.

2. The apparatus according to claim 1 wherein one or more of said surface features comprises a surface projection.

3. The apparatus according to claim 2 wherein said surface projection is a pin.

4. The apparatus according to claim 1 wherein one or more of said surface features comprises a surface contour.

5. The apparatus according to claim 4 wherein said surface contour comprises a radius of curvature sufficient to secure to locally secure the implant forming material such that the implant forming material is permanently deformed under application of suitable pressure.

6. The apparatus according to claim 1 wherein one or more of said surface features are positioned outside of a region associated with said defect.

7. The apparatus according to claim 1 wherein one or more of said surface features are positioned, at least in part, within a region associated with said defect.

8. The apparatus according to claim 1 wherein said mold and said forming tool comprise a patient-specific surface profile.

9. The apparatus according to claim 8 wherein said patient-specific surface profile is based on imaging data.

10. The apparatus according to claim 1 wherein a positive surface feature in one of said mold and said forming tool corresponds to a negative surface feature in the other of said mold and said forming tool.

11. The apparatus according to claim 1 wherein one or more of said surface features comprises an anatomical surface feature.

12. The apparatus according to claim 11 wherein said anatomical surface feature is a rim or a ridge.

13. The apparatus according to claim 12 wherein the rim the orbital rim.

14. The apparatus according to claim 12 wherein the ridge is selected from the group consisting of brow ridges, zygomatic processes, maxillary buttresses, and a margin of a mandible.

15. The apparatus according to claim 11 wherein said anatomical surface feature is augmented with an artificial surface feature.

16. The apparatus according to claim 1 wherein one or more of said surface features comprises an artificial surface feature.

17. The apparatus according to claim 16 wherein said artificial surface feature is selected from the group consisting of divots with corresponding projections, an edge over which the implant forming material may be folded and stretched, a groove and matching ridge, and a groove comprising inter-digitated teeth with a matching ridge.

18. The apparatus according to claim 1 wherein one or more of said mold and said forming tool further comprises an additional anatomical feature for indirect verification of registration of the implant forming material.

19. The apparatus according to claim 18 where said additional anatomical feature is selected from the group consisting of cranial suture lines and muscle attachments.

20. The apparatus according to claim 1 wherein said defect is a cranial defect.

21. The apparatus according to claim 1 wherein one or more of said surface features is secured onto or recessed within said mold or forming tool.

22. An apparatus for shaping an implant forming material into a surgical implant for correcting a defect in a skeletal region, the implant forming material comprising a solid deformable structure, wherein the implant forming material supports lateral fluid flow when the implant forming material is compressed between two surfaces, said apparatus comprising:
a mold comprising a defect-free surface profile of the skeletal region; and;
a forming tool having a negative surface profile relative to said mold, such that the implant forming material is shaped into the surgical implant when the implant forming material is compressed between said mold and said forming tool;
wherein one of said mold and said forming tool comprises a channel, said channel comprising an external port and an internal port, wherein said internal port is in flow communication with the implant forming material when the implant forming material is compressed between said mold and said forming tool;
wherein at least one of said mold and said forming tool comprise two or more non-adjacent surface features; and
wherein each surface feature is configured to produce fixation of a portion of the implant forming material at a location associated with said each surface feature when the implant forming material is compressed between said mold and said forming tool, such that the implant forming material is stretched between said surface features and permanently deformed beyond its elastic limit under application of suitable pressure.

23. The apparatus according to claim 22 further comprising a reservoir in flow communication with a fluid overflowing from the implant forming material when the fluid is injected into said external port.

24. The apparatus according to claim 23 further comprising a flow mechanism in fluid communication with said external port and said reservoir.

25. The apparatus according to claim 22 wherein said channel is a first channel provided within one of said mold and said forming tool, and wherein another of said mold and said forming tool comprises a second channel, wherein said second channel comprises an additional external port and an additional internal port, and wherein said additional internal port is in flow communication with the implant forming material.

26. The apparatus according to claim 25 wherein said additional external port is in flow communication with a reservoir.

27. An apparatus for shaping an implant forming material into a surgical implant for correcting a defect in a skeletal region, the implant forming material comprising a solid deformable structure, said apparatus comprising:
a mold comprising a defect-free surface profile of the skeletal region; and;
a forming tool having a negative surface profile relative to said mold, such that the implant forming material is shaped into the surgical implant when the implant forming material is compressed between said mold and said forming tool; and
a reservoir positioned to immerse the implant forming material in a liquid while the implant forming material is compressed between said mold and said forming tool;
wherein at least one of said mold and said forming tool comprise two or more non-adjacent surface features; and
wherein each surface feature is configured to produce fixation of a portion of the implant forming material at a location associated with said each surface feature when the implant forming material is compressed between said mold and said forming tool, such that the implant forming material is stretched between said surface features and permanently deformed beyond its elastic limit under application of suitable pressure.

28. The apparatus according to claim 27 wherein one of said mold and said forming tool comprises said reservoir.

29. The apparatus according to claim 27 wherein said reservoir comprises one or more retaining structures for receiving the implant forming material and preventing buoyant motion of the implant forming material when the implant forming material is contacted with the liquid.

30. The apparatus according to claim 27 further comprising a heat source for heating the liquid in said reservoir.

31. The apparatus according to claim 27 further comprising a first support for supporting said mold, a second support for supporting said forming tool, and a pressure application means for compressing the implant forming material between said mold and said forming tool.

* * * * *